United States Patent [19]

Findeisen et al.

[11] Patent Number: 5,552,369
[45] Date of Patent: Sep. 3, 1996

[54] SULPHONYLAMINOCARBONYLTRIA-ZOLINONES

[75] Inventors: Kurt Findeisen; Karl-Heinz Linker, both of Leverkusen; Joachim Kluth, Langenfeld; Klaus-Helmut Müller, Düsseldorf; Hans-Jochem Riebel, Wuppertal; Klaus König, Odenthal; Hans-Joachim Santel, Leverkusen; Robert R. Schmidt, Bergisch Gladbach, all of Germany

[73] Assignee: Bayer Aktiengesellschaft, Leverkusen, Germany

[21] Appl. No.: 411,718

[22] PCT Filed: Oct. 4, 1993

[86] PCT No.: PCT/EP93/02706

§ 371 Date: Apr. 7, 1995

§ 102(e) Date: Apr. 7, 1995

[87] PCT Pub. No.: WO94/08979

PCT Pub. Date: Apr. 28, 1994

[30] Foreign Application Priority Data

Oct. 15, 1992 [DE] Germany .................. 42 34 801.3

[51] Int. Cl.$^6$ .................. A01N 47/38; A01N 57/32; C07D 249/12; C07D 413/04
[52] U.S. Cl. .................. 504/273; 504/196; 504/197; 504/225; 504/248; 544/132; 546/210; 548/112; 548/263.2; 548/263.4; 548/263.8; 548/264.6
[58] Field of Search .................. 504/196, 197, 504/225, 248, 273; 544/132; 546/210; 548/112, 263.2, 263.4, 263.8, 264.6

[56] References Cited

U.S. PATENT DOCUMENTS

| | | | |
|---|---|---|---|
| 5,057,144 | 10/1991 | Daum et al. | 71/92 |
| 5,085,684 | 2/1992 | Muller et al. | 71/92 |
| 5,238,910 | 8/1993 | Muller et al. | 504/273 |

Primary Examiner—Patricia L. Morris
Attorney, Agent, or Firm—Sprung Horn Kramer & Woods

[57] ABSTRACT

The invention relates to new sulphonylaminocarbonyltriazolinones of the formula (I)

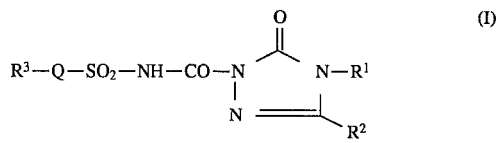

in which

Q represents oxygen, sulphur or one of the following groups

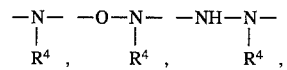

(in which the radicals $R^1$, $R^2$, $R^3$ and $R^4$ have the meanings given in the description), as well as to salts of compounds of the formula (I), to processes and novel intermediates for the preparation of the novel compounds, and to their use as herbicides.

5 Claims, No Drawings

SULPHONYLAMINOCARBONYLTRIAZOLINONES

The invention relates to new sulphonylaminocarbonyltriazolinones, to a plurality of processes and novel intermediates for their preparation, and to their use as herbicides.

It has already been disclosed that certain sulphonylaminocarbonyltriazolinones, such as, for example, 4,5-dimethyl-2-(2-chlorophenylsulphonyl-aminocarbonyl)-2,4-dihydro-3H-1,2,4-triazol-3-one, have herbicidal properties (cf. EP-A 341489/LeA 26062; cf. also EP-A 422469/LeA 27154; EP-A 425948/LeA 27155; EP-A 431291/LeA 27156). However, the activity of these compounds is not in all respects satisfactory.

There have now been found the new sulphonylaminocarbonyltriazolinones of the general formula (I)

$$R^3-Q-SO_2-NH-CO-N\begin{array}{c}O\\||\\\end{array}N-R^1 \quad (I)$$

in which

Q represents oxygen, sulphur or one of the following groups $$-N-\underset{R^4}{|},\quad -O-N-\underset{R^4}{|},\quad -NH-N-\underset{R^4}{|},$$

$R^1$ represents hydrogen, hydroxyl, amino, alkylideneamino, or represents a radical from the series consisting of alkyl, alkenyl, alkinyl, cycloalkyl, aralkyl, aryl, alkoxy, alkenyloxy, alkylamino, cycloalkylamino, dialkylamino, alkanoylamino and alkoxycarbonylamino, each of which is optionally substituted, $R^2$ represents hydrogen, hydroxyl, mercapto, amino, halogen, or represents a radical from the series consisting of alkyl, cycloalkyl, alkenyl, cycloalkenyl, aralkyl, aryl, alkoxy, alkenyloxy, alkinyloxy, cycloalkyloxy, aryloxy, aralkyloxy, alkylthio, alkylsulphinyl, alkylsulphonyl, alkenylthio, alkinylthio, cycloalkylthio, arylthio, aralkylthio, alkylamino, alkenylamino, arylamino, aralkylamino, dialkylamino, aziridino, pyrrolidino, piperidino or morpholino, each of which is optionally substituted, $R^3$ represents a radical from the series consisting of alkyl, alkenyl, alkinyl, cycloalkyl, cycloalkylalkyl, alkylsulphonyl, alkylaminosulphonyl, dialkylaminosulphonyl, aryl and aralkyl, each of which is optionally substituted, $R^4$ represents hydrogen, hydroxyl, amino, cyano, alkoxycarbonyl, or represents alkyl, alkenyl, alkinyl, alkoxy, alkenyloxy, aralkoxy, aryloxy or dialkoxy(thio)phosphoryl, each of which is optionally substituted, or the following group $Q^1-R^5$, in which
  $Q^1$ represents —CO— or —SO$_2$— and
  $R^5$ represents alkyl, cycloalkyl or aryl, each of which is optionally substituted, and salts of compounds of the formula (I).

The new sulphonylaminocarbonyltriazolinones of the formula (I) are obtained when (a) chlorosulphonylaminocarbonyltriazolinones of the general formula (II)

$$Cl-SO_2-NH-CO-N\begin{array}{c}O\\||\\\end{array}N-R^1 \quad (II)$$

in which
  $R^1$ and $R^2$ have the abovementioned meaning, are reacted with nucleophilic compounds of the general formula (III)

$$R^3-Q-H \quad (III)$$

in which
  Q and $R^3$ have the abovementioned meaning, if appropriate in the presence of an acid acceptor and if appropriate in the presence of a diluent, or when (b) triazolinones of the general formula (IV)

$$H-N\begin{array}{c}O\\||\\\end{array}N-R^1 \quad (IV)$$

in which
  $R^1$ and $R^2$ have the abovementioned meaning, are reacted with chlorosulphonyl isocyanate, if appropriate in the presence of a diluent, and the resulting chlorosulphonylaminocarbonyltriazolinones of the formula (II)—above—are reacted, without intermediate isolation, with nucleophilic compounds of the general formula (III)—above—if appropriate in the presence of an acid acceptor and if appropriate in the presence of a diluent, and, if appropriate, the compounds of the formula (I) obtained by process (a) or (b) are convened to salts by customary methods.

Other methods which are possible for the preparation of the compounds of the formula (I) according to the invention are given below, Q, $R^1$, $R^2$ and $R^3$ in each case having the abovementioned meaning:

(c) Reaction of isocyanates of the formula (V) with triazolinones of the formula (IV):

$$R^3-Q-SO_2-N=C=O \quad (V) +$$

$$H-N\begin{array}{c}O\\||\\\end{array}N-R^1 \quad (IV) \longrightarrow$$

$$R^3-Q-SO_2-NH-CO-N\begin{array}{c}O\\||\\\end{array}N-R^1 \quad (I)$$

(d) Reaction of aminosulphonyl compounds of the formula (VI) with oxycarbonyltriazolinones of the formula (VII) (R: alkyl, aralkyl, aryl):

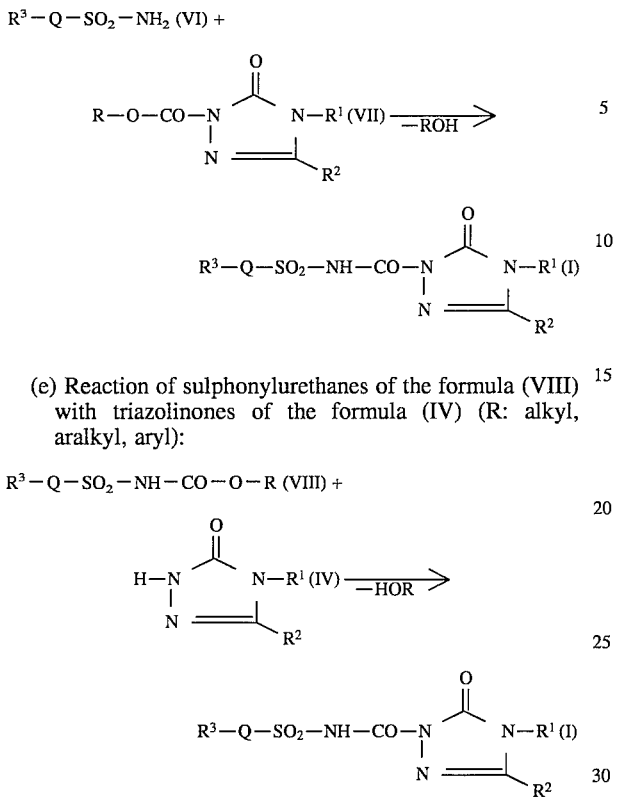

(e) Reaction of sulphonylurethanes of the formula (VIII) with triazolinones of the formula (IV) (R: alkyl, aralkyl, aryl):

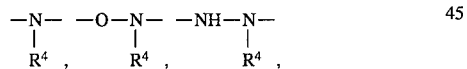

The new sulphonylaminocarbonyltriazolinones of the general formula (I) are distinguished by a powerful herbicidal activity.

Surprisingly, the new compounds of the formula (I) display a considerably more powerful herbicidal activity than 4,5-dimethyl-2-(2-chlorophenylsulphonyl-aminocarbonyl)-2,4-dihydro-3H-1,2,4-triazol-3-one, which is known and which has a similar structure.

The invention preferably relates to compounds of the formula (I) in which

Q represents oxygen, sulphur or one of the following groups $$-\underset{R^4}{N}-\quad -O-\underset{R^4}{N}-\quad -NH-\underset{R^4}{N}-$$

$R^1$ represents hydrogen, hydroxyl, amino, or represents $C_2$–$C_{10}$-alkylideneamino, or represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, or represents $C_3$–$C_6$-alkenyl or $C_3$–$C_6$-alkinyl, each of which is optionally substituted by fluorine, chlorine and/or bromine, or represents $C_3$–$C_6$-cycloalkyl which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxy-carbonyl, or represents $C_1$–$C_6$-alkoxy which is optionally substituted by fluorine, chlorine, cyano, phenyl, $C_1$–$C_4$-alkoxy or $C_1$–$C_4$-alkoxy-carbonyl, or represents $C_3$–$C_6$-alkenyloxy, or represents $C_1$–$C_4$-alkylamino, $C_3$–$C_6$-cycloalkylamino or di-($C_1$–$C_4$-alkyl)-amino, each of which is optionally substituted by fluorine, cyano, $C_1$–$C_4$-alkoxy or $C_1$–$C_4$-alkoxy-carbonyl, or represents $C_1$–$C_6$-alkanoylamino, or represents $C_1$–$C_6$-alkoxycarbonylamino, $R^2$ represents hydrogen, hydroxyl, mercapto, amino, halogen, or represents $C_1$–$C_6$-alkyl or $C_2$–$C_6$-alkenyl, optionally substituted by fluorine, chlorine, bromine cyano, $C_3$–$C_6$-cycloalkyl, $C_1$–$C_4$-alkoxy, $C_1$–$C_4$-alkylthio or $C_1$–$C_4$-alkoxycarbonyl, or represents $C_3$–$C_6$-cycloalkyl which is optionally substituted by fluorine, chlorine, bromine and/or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy and/or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxy-carbonyl, or represents $C_1$–$C_6$-alkoxy which is optionally substituted by fluorine, chlorine, cyano, $C_1$–$C_4$-alkoxy or $C_1$–$C_4$-alkoxy-carbonyl, or represents $C_3$–$C_6$-alkenyloxy, $C_3$–$C_6$-alkinyloxy or $C_3$–$C_6$-cycloalkyloxy, or represents phenoxy or benzyloxy, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents $C_1$–$C_6$-alkylthio, $C_1$–$C_6$-alkylsulphinyl, $C_1$–$C_6$-alkylsulphonyl, $C_3$–$C_6$-alkenylthio, $C_3$–$C_6$-alkinylthio or $C_3$–$C_6$-cycloalkylthio, each of which is optionally substituted by fluorine, chlorine, cyano, $C_1$–$C_4$-alkoxy or $C_1$–$C_4$-alkoxy-carbonyl, or represents phenylthio or benzylthio, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents $C_1$–$C_6$-alkylamino or $C_3$–$C_6$-alkenylamino, or represents phenylamino or benzylamino, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents di-($C_1$–$C_4$-alkyl)-amino, or represents aziridino, pyrrolidino or morpholino, each of which is optionally substituted by $C_1$–$C_4$-alkyl, $R^3$ represents $C_1$–$C_6$-alkyl, $C_3$–$C_6$-alkenyl or $C_3$–$C_6$-alkinyl, each of which is optionally substituted by halogen, cyano, carboxyl, $C_1$–$C_4$-alkoxy, $C_1$–$C_4$-alkylthio, $C_1$–$C_4$-alkylsulphinyl, $C_1$–$C_4$-alkylsulphonyl or $C_1$–$C_4$-alkoxy-carbonyl, or represents $C_3$–$C_6$-cycloalkyl or $C_3$–$C_6$-cycloalkyl-$C_1$–$C_4$-alkyl, each of which is optionally substituted by halogen, cyano, carboxyl, $C_1$–$C_4$-alkyl, $C_1$–$C_4$-halogenoalkyl or $C_1$–$C_4$-alkoxy-carbonyl, or represents $C_1$–$C_6$-alkylsulphonyl, $C_1$–$C_6$-alkylaminosulphonyl or di-($C_1$–$C_4$-alkyl)-aminosulphonyl, each of which is optionally substituted by halogen, or represents phenyl, naphthyl, tetralinyl, phenyl-$C_1$–$C_4$-alkyl, naphthyl-$C_1$–$C_4$-alkyl or tetralinyl-$C_1$–$C_4$-alkyl, each of which is optionally substituted by halogen, cyano, carboxyl, nitro, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (in each case optionally substituted by halogen, cyano, $C_1$–$C_4$- alkoxy or $C_1$–$C_4$-alkoxy-carbonyl), by $C_1$–$C_4$-alkylsulphonyloxy, $C_1$–$C_4$-alkylaminosulphonyloxy, di-($C_1$–$C_4$-alkyl)aminosulphonyloxy, $C_1$–$C_4$-halogenoalkylsulphonyloxy, di-($C_1$–$C_4$-alkyl)-aminocarbonyl or $C_1$–$C_4$-alkylaminocarbonyloxy, by $C_3$–$C_6$-cycloalkyl or $C_3$–$C_6$-cycloalkyl-$C_1$–$C_4$-alkyl (in each case optionally substituted by halogen or $C_1$–$C_4$-alkyl), by phenyl, phenoxy, phenylthio, phenylsulphinyl, phenylsulphonyl, phenylsulphonyloxy, phenylamino, phenylcarbonyl or phenyl-$C_1$–$C_4$-alkyl (in each case optionally substituted by halogen, cyano, nitro, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkythio, $C_1$–$C_4$-halogenoalkylthio, $C_1$–$C_4$-alkoxy-carbonyl or $C_1$–$C_4$-alkoxyamino), by $C_1$–$C_4$-alkyl-carbonyl, $C_3$–$C_6$-cycloalkylcarbonyl or $C_1$–$C_4$-alkoxy-carbonyl (in each case optionally substituted by halogen, $C_3$–$C_6$-cycloalkyl or $C_1$–$C_4$-alkoxy), $R^4$ represents hydrogen, hydroxyl, amino, cyano, or represents $C_1$–$C_6$-alkyl, $C_3$–$C_6$-alkenyl or $C_3$–$C_6$-alkinyl, each of which is optionally substituted by halogen, cyano, carboxyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylamino, di-($C_1$–$C_4$-alkyl)-amino or $C_1$–$C_4$-alkoxycarbonyl, or represents $C_1$–$C_4$-alkoxy-carbonyl, or represents $C_1$–$C_6$-alkoxy, $C_3$–$C_6$-alkenyloxy, benzyloxy, phenoxy or di-($C_1$–$C_4$-alkoxy)-(thio)-phosphoryl, or represents the following group $Q^1$—$R^5$ in which
$Q^1$ represents —CO— or —$SO_2$— and
$R^5$ represents $C_1$–$C_6$-alkyl which is optionally substituted by halogen or $C_1$–$C_4$-alkoxy, or represents $C_3$–$C_6$-cycloalkyl which is optionally substituted by halogen or $C_1$–$C_4$-alkyl, or represents phenyl which is optionally substituted by halogen, $C_1$–$C_4$-alkyl, $C_1$–$C_4$-halogenoalkyl or $C_1$–$C_4$-alkoxy.

The invention furthermore preferably relates to the sodium, potassium, magnesium, calcium, ammonium, $C_1$–$C_4$-alkylammonium, di-($C_1$–$C_4$-alkyl)-ammonium, tri-($C_1$–$C_4$-alkyl)-ammonium, $C_5$- or $C_6$-cycloalkylammonium and di-($C_1$–$C_2$-alkyl)-benzylammonium salts of compounds of the formula (I) in which Q, $R^1$, $R^2$ and $R^3$ have the meanings mentioned above as being preferred.

In particular, the invention relates to compounds of the formula (I), in which

Q represents oxygen or the group

$R^1$ represents hydrogen, hydroxyl, amino, or represents $C_3$–$C_8$-alkylideneamino, or represents methyl, ethyl, n- or i-propyl, n-, i-, s- or t-butyl, dichloromethyl, fluoroethyl, chloroethyl, difluoroethyl, dichloroethyl, trifluoroethyl, trichloroethyl, chlorodifluoroethyl, tetrafluoroethyl, cyanomethyl; cyanoethyl, methoxymethyl, ethoxymethyl, methoxyethyl, ethoxyethyl, or represents allyl, chloroallyl, dichloroallyl, propargyl, or represents chloropropyl, benzyl or phenyl, or represents methoxy, ethoxy, n- or i-propoxy, or represents allyloxy, n- or i- or s-butoxy, or represents methylamino, ethylamino, n- or i-propylamino, or represents cyclopropylamino, dimethylamino, diethylamino, acetylamino, methoxycarbonylamino or ethoxycarbonylamino, $R^2$ represents hydrogen, hydroxyl, mercapto, amino, fluorine, chlorine, bromine, or represents methyl, ethyl, n- or i-propyl, n-, i-, s- or t-butyl, difluoromethyl, trifluoromethyl, dichloromethyl, trichloromethyl, cyanomethyl, cyanoethyl, cyclopropylmethyl, methoxymethyl, ethoxymethyl, methoxyethyl, ethoxyethyl, methylthiomethyl, ethylthiomethyl, methylthioethyl or ethylthioethyl, or represents cyclopropyl, difluorocyclopropyl or dichlorocyclopropyl, or represents phenyl or benzyl, or represents methoxy, ethoxy, n- or i-propoxy, or represents methoxymethoxy, ethoxymethoxy, methoxyethoxy or ethoxy-ethoxy, or represents phenoxy or benzyloxy, or represents methylthio, ethylthio, n- or i-propylthio, alkylthio, propargylthio, cyclopropylmethylthio, methylsulphinyl, ethylsulphinyl, methylsulphonyl, ethylsulphonyl, phenylthio or benzylthio, or represents methylamino, ethylamino, n- or i-propylamino, phenylamino or benzylamino, or represents dimethylamino, diethylamino, dipropylamino, methylethylamino, methylpropylamino, or represents aziridino, or represents pyrrolidino, piperidino or morpholino, each of which is optionally substituted by methyl or ethyl, $R^3$ represents methyl, ethyl, n- or i-propyl or n-, i-, s- or t-butyl, each of which is optionally substituted by fluorine, chlorine, cyano, methoxy, ethoxy, methoxycarbonyl or ethoxycarbonyl, or represents cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl or cyclohexylethyl, each of which is optionally substituted by fluorine, chlorine, cyano, methyl, ethyl, trifluoromethyl, methoxycarbonyl or ethoxycarbonyl, or represents methylsulphonyl, ethylsulphonyl, propylsulphonyl or butylsulphonyl, optionally substituted by fluorine or chlorine, or represents phenyl which is optionally substituted by fluorine, chlorine, bromine, cyano, carboxyl, nitro, by methyl, ethyl, methoxy, ethoxy, methylthio, ethylthio, methylsulphinyl, ethylsulphinyl, methylsulphonyl or ethylsulphonyl (in each case optionally substituted by fluorine, chlorine, cyano, methoxy, ethoxy, methoxycarbonyl or ethoxycarbonyl), by methylsulphonyloxy, ethylsulphonyloxy, methylaminosulphonyloxy, ethylaminosulphonyloxy, dimethylaminosulphonyloxy, diethylaminosulphonyloxy, trifluoromethylsulphonyloxy, dimethylaminocarbonyl or diethylaminocarbonyl, by cyclohexyl or cyclohexylmethyl (in each case optionally substituted by chlorine, methyl or ethyl), by phenyl, phenoxy, phenylthio, phenylsulphonyl, phenylsulphonyloxy, phenylamino, phenylcarbonyl, phenylmethyl or phenylethyl (in each case optionally substituted by fluorine, chlorine, cyano, nitro, methyl, ethyl, trifluoromethyl, methoxy, ethoxy, difluoromethoxy, trifluoromethoxy, methylthio, ethylthio, trifluoromethylthio, methoxycarbonyl or ethoxycarbonyl), by acetyl, cyclopropylcarbonyl, methoxycarbonyl or ethoxycarbonyl (optionally substituted by fluorine, chlorine, cyclopentyl, cyclohexyl, methoxy or ethoxy), or represents naphthyl or tetralinyl, each of which is optionally substituted by fluorine, chlorine, cyano, nitro, methyl, ethyl, methoxy or ethoxy, or represents naphthylmethyl, naphthylethyl, tetralinylmethyl or tetralinylethyl, each of which is optionally substituted by fluorine, chlorine, methyl, ethyl, methoxy or ethoxy, $R^4$ represents hydrogen, cyano, cyanomethyl, cyanoethyl, difluoromethyl, methoxymethyl, ethoxymethyl, methoxyethyl, ethoxyethyl, methoxycrbonylmethyl, ethoxycarbonylmethyl, methoxycarbonylethyl, ethoxycarbonylethyl, allyl, propargyl, methoxycarbonyl, ethoxycarbonyl, methoxy, ethoxy, allyloxy or benzyloxy, or represents the group $Q^1$—$R^5$ in which $Q^1$ represents —CO— or —$SO_2$— and $R^5$ represents methyl, ethyl or propyl, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl or ethyl, or represents phenyl which is optionally substituted by fluorine, chlorine, bromine, methyl, ethyl, trifluoromethyl, methoxy or ethoxy.

The definitions of radicals mentioned above, in general or where preferred ranges are mentioned, apply to the end products of the formula (I) and, analogously, to the starting materials or intermediates required in each case for the preparation. These definitions of radicals can be combined with each other as desired, that is to say combinations between the preferred ranges indicated are also possible.

The hydrocarbon radicals mentioned in the definitions of the radicals, such as alkyl, alkenyl or alkinyl, also in combinations with hetero atoms, such as in alkoxy, alkylthio or alkylamino, are straight-chain or branched, even when this is not expressly stated.

Halogen generally represents fluorine, chlorine, bromine or iodine, preferably fluorine, chlorine or bromine, in particular fluorine or chlorine.

Examples of the compounds of the formula (I) according to the invention are listed in Table 1 below.

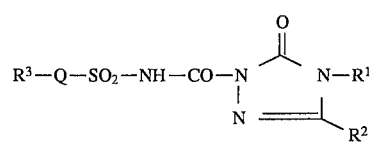

(I)

TABLE 1

| Q | $R^1$ | $R^2$ | $R^3$ |
|---|---|---|---|
| O | $CH_3$ | $C_2H_5$ | $n$-$C_3H_7$ |
| NH | $CH_3$ | $C_2H_5$ | $i$-$C_3H_7$ |
| O | $C_2H_5$ | $C_2H_5$ | 2-F-phenyl |
| NH | $OCH_3$ | $n$-$C_3H_7$ | $i$-$C_4H_9$ |
| NH | $OC_2H_5$ | $CH_3$ | cyclopropyl |
| $NCH_3$ | $CH_3$ | $i$-$C_3H_7$ | —$CH_2$-cyclohexyl |
| NH | $C_2H_5$ | cyclopropyl | 4-$COOC_2H_5$-phenyl |
| NH | cyclopropyl | $C_2H_5$ | —$CH_2$-(4-Cl-phenyl) |

TABLE 1-continued

| Q | $R^1$ | $R^2$ | $R^3$ |
|---|---|---|---|
| NH | $C_2H_5$ | $SCH_3$ | 2-Br-phenyl |
| NH | $C_2H_5$ | $OC_2H_5$ | 3,4-di-$OCH_3$-phenyl |
| $NCH_3$ | $OCH_3$ | $OCH_3$ | $n$-$C_4H_9$ |
| NH | cyclopropyl | $SCH_3$ | —CH($CH_3$)-phenyl |
| NH | cyclopropyl | $OC_2H_5$ | 2-$COOCH_3$-phenyl |
| NH | $C_2H_5$ | $OCH_3$ | cyclopentyl |
| $NCH_3$ | $CH_3$ | $OC_2H_5$ | 2-$OCHF_2$-phenyl |
| NH | $C_2H_5$ | $SC_2H_5$ | 2,4-di-F-phenyl |
| O | $OC_2H_5$ | $C_2H_5$ | 4-$COOCH_3$-phenyl |
| NH | $CH_3$ | $SC_2H_5$ | 3-$SC_2H_5$-phenyl |
| NH | $C_2H_5$ | $OC_2H_5$ | 3-$CF_3$-phenyl |
| NH | $CH_3$ | cyclopropyl | 4-$COOC_2H_5$-phenyl |

TABLE 1-continued

Examples of the compounds of the formula (I)

| Q | R¹ | R² | R³ |
|---|---|---|---|
| NH | CH₃ | CH₃ | -C₆H₄-C₆H₅ (o) |
| NH | C₂H₅ | cyclopropyl | -C₆H₄-Cl (o) |
| NH | cyclopropyl | OCH₃ | -CH₂-C₆H₃(OCH₃)₂ |
| NH | OCH₃ | cyclopropyl | -CH₂COOC₂H₅ |
| NH | C₂H₅ | N(CH₃)₂ | -C₆H₄-SCH₃ |
| NH | C₂H₅ | -N(aziridinyl) | -CH(CN)-C₆H₅ |
| O | C₂H₅ | Cl | -CH(CH₃)COOC₂H₅ |
| NH | CH₃ | Br | -C₆H₄-CH₃ |
| NH | CH₃ | i-OC₃H₇ | -C₆H₄-CN |
| O | C₂H₅ | N(CH₃)₂ | -C₆H₄-OC₂H₅ |
| NH | CH₃ | -CH₂SC₂H₅ | -CH₂CH₂OC₂H₅ |

If, for example, 2-chlorosulphonylaminocarbonyl-4-ethoxy-5-ethyl-2,4-dihydro-3H-1,2,4-triazol-3-one and 2-fluoro-phenol are used as starting substances, the course of the reaction in process (a) according to the invention can be outlined by the following equation:

+

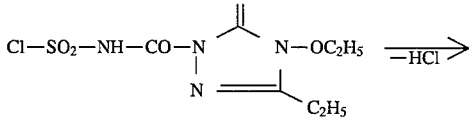

-continued

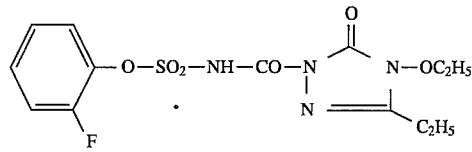

If, for example, 4-ethyl-5-ethylthio-2,4-dihydro-3H-1,2,4-triazol-3-one and chlorosulphonyl isocyanate and then methyl 2-amino-benzoate are used as starting substances, the course of the reaction in process (b) according to the invention can be outlined by the following equation:

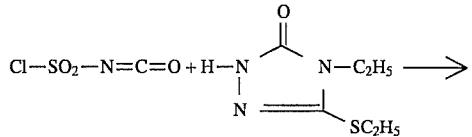

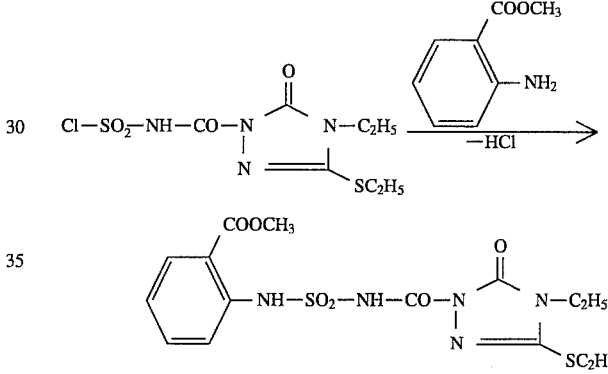

Formula (II) provides a general definition of the chlorosulphonylaminocarbonyltriazolinones to be used as starting substances in process (a) according to the invention for the preparation of compounds of the formula (I).

In formula (II), R¹ and R² preferably, or in particular, have those meanings which have already been mentioned above in connection with the description of the compounds of the formula (I) according to the invention as being preferred, or particularly preferred, for R¹ and R².

The following may be mentioned as examples of the starting substances of the formula (II):

4,5-dimethyl-, 4,5-diethyl-, 4-ethyl-5-methyl-, 5-ethyl-4-methyl-, 4-methyl-5-propyl-, 4-ethyl-5-propyl-, 4-cyclopropyl-5-ethyl-, 5-cyclopropyl-4-methyl-, 5-cyclopropyl-4-ethyl-, 4-methyl-5-chloro-, 4-ethyl-5-chloro-, 4-methyl-5-bromo-, 4-ethyl-5-bromo-, 4-cyclopropyl-5-chloro-, 4-cyclopropyl-5-bromo-, 4-methoxy-5-methyl-, 4-ethoxy-5-methyl-, 4-ethoxy-5-ethyl-, 4-methoxy-5-ethyl-, 4-methyl-5-methoxy-, 4-ethyl-5-methoxy-, 4-methyl-5-ethoxy-, 4-ethyl-5-ethoxy-, 4-methyl-5-methylthio-, 4-methyl-5-ethylthio-, 4-ethyl-5-methylthio-, 4-ethyl-5-ethylthio, 4-cyclopropyl-5-methoxy-, 4-cyclopropyl-5-ethoxy-, 4-cyclopropyl-5-methylthio-, 4-cyclopropyl-5-ethylthio-, 4-methoxy-, 5-cyclopropyl-,4-ethoxy-5-cyclopropyl-,4-methoxy-5-ethoxy-,4,5-dimethoxy-, 4,5-diethoxy-, 4-methyl-5-dimethylamino-, 4-ethyl-5-dimethylaminoand 4-cyclopropyl-5-dimethylamino-2-chlorosulphonylaminocarbonyl-2,4-dihydro-3H-1,2,4-triazol-3-one.

The chlorosulphonylaminocarbonyltriazolinones of the general formula (II) are as yet unknown from the literature and, being new substances, also a subject-matter of the present invention.

The new compounds of the formula (II) are obtained when triazolinones of the general formula (IV)

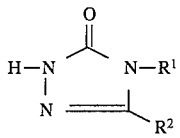

(IV)

in which

R¹ and R² have the abovementioned meaning are reacted with chlorosulphonyl isocyanate at temperatures of between −20° C. and +50° C., if appropriate in the presence of a diluent such as, for example, methylene chloride, and the product is worked up in the customary manner (cf. the preparation examples).

Formula (III) provides a general definition of the nucleophilic compounds to be used as starting substances in processes (a) and (b) according to the invention for the preparation of compounds of the formula (I).

In formula (III) Q and R³ preferably, or in particular, have those meanings which have already been mentioned above in connection with the description of the compounds of the formula (I) according to the invention as being preferred, or particularly preferred, for Q and R³.

The starting substances of the formula (III) are known chemicals for organic synthesis.

Formula (IV) provides a general definition of the triazolinones to be used as starting substances in processes (a) and (b) according to the invention for the preparation of compounds of the formula (I).

In formula (IV) R¹ and R² preferably, or in particular, have those meanings which have already been mentioned above in connection with the description of the compounds of the formula (I) according to the invention as being preferred, or particularly preferred, for R¹ and R².

The starting substances of the formula (IV) are known and/or can be prepared by processes known per se (cf. EP-A 283876, EP-A 294666, EP-A 301946, EP-A 298371, EP-A 341489, EP-A 399294, EP-A 398096, EP-A 422469, EP-A 425948, EP-A 431291, EP-A 477646, DE-OS 4110795 (German Published Specification).

Processes (a) and (b) according to the invention for the preparation of the new compounds of the formula (I) are preferably carried out using diluents. Suitable diluents are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether, glycol dimethyl ether, diglycol dimethyl ether, tetrahydrofuran and dioxane, ketones such as acetone, methyl ethyl ketone, methyl isopropyl ketone, methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

Acid acceptors which can be employed in processes (a) and (b) according to the invention are all acid-binding agents which can conventionally be used for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, sodium tert-butylate and potassium tert-butylate, furthermore basic nitrogen compounds such as Trimethylamine, Triethylamine, Tripropylamine, Tributylamine, Diisobutylamine, Dicyclohexylamine, Ethyldiisopropylamine, Ethyldicyclohexylamine, N,N-Dimethylbenzylamine, N,N-Dimethyl-aniline, Pyridine, 2-Methyl-, 3-Methyl-, 4-Methyl-, 2,4-Dimethyl-, 2,6-Dimethyl-, 2-Ethyl-, 4-Ethyl- and 5-Ethyl-2-methyl-pyridine, 1,5-Diazabicyclo-[4,3,0]-non-5-en (DBN), 1,8-Diazabicyclo-[5,4,0]-undec-7-en (DBU) and 1,4-Diazabicyclo-[2,2,2]-octane (DABCO).

When carrying out processes (a) and (b) according to the invention, the reaction temperatures can be varied within a substantial range. In general, the processes are carried out at temperatures between −20° C. and +80° C., preferably at temperatures between −10° C. and +50° C.

Processes (a) and (b) according to the invention are generally carried out under atmospheric pressure. However, it is also possible to carry out the processes under elevated or reduced pressure.

To carry out processes (a) and (b) according to the invention, the starting substances required in each case are generally employed in approximately equimolar amounts. However, one of the components employed in each case may also be used in a larger excess. In general, the reactions are carried out in a suitable diluent in the presence of an acid acceptor, and the reaction mixture is stirred for several hours at the temperature required in each case. Working-up in processes (a) and (b) according to the invention is carried out in each case by customary methods (cf. the preparation examples).

If appropriate, salts may be prepared from the compounds of the general formula (I) according to the invention. Such salts are obtained in a simple fashion by customary salt formation methods, for example by dissolving or dispersing a compound of the formula (I) in a suitable solvent such as, for example, methylene chloride, acetone, tertbutyl methyl ether or toluene, and adding a suitable base. The salts can then be isolated by concentration or filtration with suction, if appropriate after prolonged stirring.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating dicotyledon weeds in monocotyledon cultures by the pre- as well as post-emergence methods.

Moreover, the active compounds (I) according to the invention also display interesting secondary actions, i.e. a leaf-acting insecticidal action, as well as fungicidal actions in particular against *Pyricularia oryzae*, for example in rice, and against *Erysiphe graminis*.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuronmethyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

Preparation Examples:

EXAMPLE 1

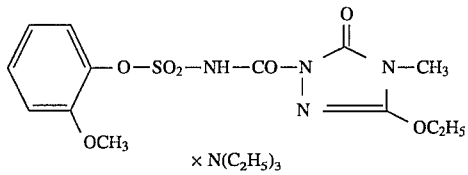

(Process (a))

2.84 g (0.01 mol) of 2-chlorosulphonylaminocarbonyl-4-methyl-5-ethoxy-2,4-dihydro-3H-1,2,4-triazol-3-one are introduced into 100 ml of methylene chloride, and 1.24 g (0.01 mol) of 2-methoxy-phenol and 2.02 g (0.02 mol) of triethylamine are added to this mixture at 20° C. The reaction mixture is stirred for 60 minutes at 20° C. It is then washed three times using 150 ml of water in each case, dried using sodium sulphate and filtered. The filtrate is concentrated under a water pump vacuum, and the residue is recrystallized from isopropanol.

2.5 g (53% of theory) of the triethylammonium salt of 2-(2-methoxy-phenoxy)sulphonylaminocarbonyl-4-methyl-5-ethoxy-2,4-dihydro-3H-1,2,4-triazol-3-one of melting point 107° C. are obtained.

EXAMPLE 2

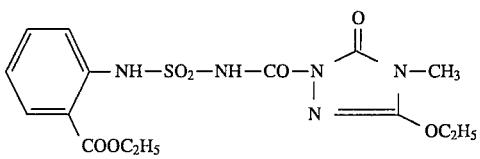

(Process (a))

5.69 g (0.02 mol) of 2-chlorosulphonylaminocarbonyl-4-methyl-5-ethoxy-2,4-dihydro-3H-1,2,4 -triazol-3-one are introduced into 150 ml of methylene chloride, and a solution of 6.6 g (0.04 mol) of ethyl 2-amino-benzoate in 20 ml of methylene chloride is added to this mixture at 20° C. The reaction mixture is stirred for 60 minutes at 20° C. It is then washed three times using 150 ml of water in each case, dried using sodium sulphate and filtered. The filtrate is concentrated under a water pump vacuum and the residue is recrystallized from isopropanol.

5.7 g (69% of theory) of 2-(2-ethoxy-carbonyl-phenylamino)-sulphonylaminocarbonyl-4-methyl-5-ethoxy-2,4-dihydro-3H-1,2,4-triazol-3-one of melting point 135° C. are obtained.

EXAMPLE 3

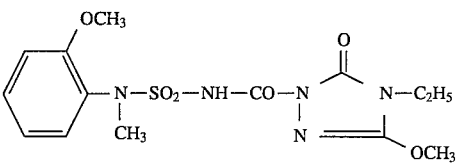

(Process (a))

5.69 g (0.02 mol) of 2-chlorosulphonylaminocarbonyl-4-ethyl-5-methoxy-2,4-dihydro-3H-1,2,4-triazol-3-one are introduced into 150 ml of methylene chloride, and a solution of 2.74 g (0.02 mol) of 2-methoxy-N-methylaniline and 2.02 g (0.02 mol) of triethylamine in 20 ml of methylene chloride is added to this mixture at 20° C. The reaction mixture is stirred for 60 minutes at 20° C. It is then washed three times using 150 ml of water in each case, dried using sodium sulphate and filtered. The filtrate is concentrated under a water pump vacuum and the residue is recrystallized from isopropanol.

3.2 g (40% of theory) of 2-(2-methoxy-N-methyl-phenylamino)-sulphonylaminocarbonyl-4-ethyl-5-methoxy-2,4-dihydro-3H-1,2,4-triazol-3-one of melting point 134° C. are obtained.

EXAMPLE 4

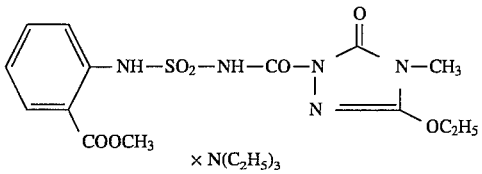

(Process (b))

4.3 g (0.03 mol) of 4-methyl-5-ethoxy-2,4-dihydro-3H-1,2,4-triazol-3-one are introduced into 150 ml of methylene chloride, and the mixture is cooled to −10° C. A solution of 4.3 g (0.03 mol) of chlorosulphonyl isocyanate in 20 ml of methylene chloride is then added, and the mixture is stirred for 30 minutes. Then, a solution of 4.53 g (0.03 mol) of methyl 2-amino-benzoate and 6.06 g (0.06 mol) of triethylamine in 20 ml of methylene chloride is added dropwise at 20° C., and the reaction mixture is stirred for a further 30 minutes. It is subsequently washed three times using 150 ml of water in each case, dried using sodium sulphate and filtered. The filtrate is concentrated under a water pump vacuum, the residue is stirred with ethyl acetate, and the product which has been obtained as crystals is isolated by filtration with suction.

11 g (73% of theory) of the triethylammonium salt of 2-(2-methoxycarbonyl-phenylamino)-sulphonylaminocarbonyl-4-methyl-5-ethoxy-2,4-dihydro-3H-1,2,4-triazol-3-one of melting point 142° C. (decomposition) are obtained.

Other examples of the compounds of the formula (I) which can be prepared analogously to Preparation Examples 1 to 4 and in accordance with the general description of the preparation processes according to the invention are those listed in Table 2 below.

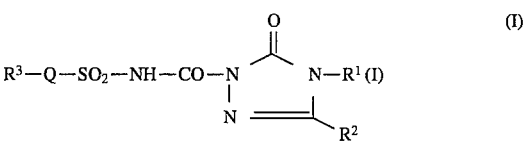

TABLE 2

Preparation examples of the compounds of the formula (I)

| Ex. No. | Q | R¹ | R² | R³ | Physical data |
|---|---|---|---|---|---|
| 5 | NH | CH₃ | CH₃ | s-C₄H₉ | m.p.: 80° C. |
| 6 | NH | CH₃ | CH₃ | 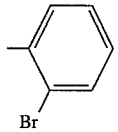 2-Br-phenyl | m.p.: 68° C. |
| 7 | NH | CH₃ | CH₃ | t-C₄H₉ | m.p.: 234° C. |
| 8 | NCH₃ | CH₃ | CH₃ | i-C₃H₇ | m.p.: 113° C. |
| 9 | NCH₃ | CH₃ | OC₂H₅ | i-C₃H₇ | m.p.: 129° C. |
| 10 | NH | CH₃ | OC₂H₅ | 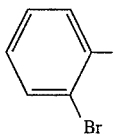 2-Br-phenyl | m.p.: 153° C. |
| 11 | NH | CH₃ | OC₂H₅ | t-C₄H₉ | m.p.: 148° C. |
| 12 | NH | CH₃ | OC₂H₅ | s-C₄H₉ | m.p.: 137° C. |
| 13 | NH | CH₃ | OC₂H₅ | 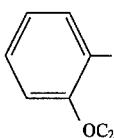 2-OC₂H₅-phenyl | m.p.: 107° C. |
| 14 | NH | CH₃ | CH₃ | 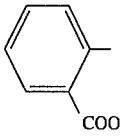 2-COOC₂H₅-phenyl | m.p.: 153° C. |
| 15 | NH | CH₃ | CH₃ | 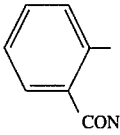 2-CON(iC₃H₇)₂-phenyl | m.p.: 140° C. Isolated in the form of the triethylammonium salt |
| 16 | NH | C₂H₅ | OCH₃ | 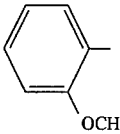 2-OCH₃-phenyl | m.p.: 111° C. |
| 17 | NH | C₂H₅ | OCH₃ | 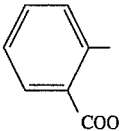 2-COOC₂H₅-phenyl | m.p.: 145° C. |
| 18 | NH | C₂H₅ | OCH₃ | 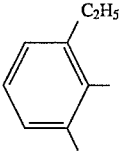 2,6-di-C₂H₅-phenyl | m.p.: 175° C. |
| 19 | NH | C₂H₅ | OCH₃ | 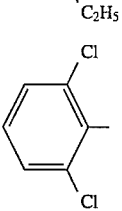 2,6-di-Cl-phenyl | m.p.: 163° C. |

TABLE 2-continued
Preparation examples of the compounds of the formula (I)
| Ex. No. | Q | R$^1$ | R$^2$ | R$^3$ | Physical data |
|---|---|---|---|---|---|
| 20 | NH | C$_2$H$_5$ | OCH$_3$ | 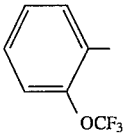 | $^1$H NMR (CDCl$_3$, δ): 3.60–3.78; 4.10; 5.30 ppm |
| 21 | NH | C$_2$H$_5$ | OCH$_3$ | 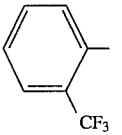 | m.p.: 148° C. |
| 22 | NH | C$_2$H$_5$ | OCH$_3$ | 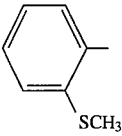 | m.p.: 133° C. |
| 23 | NH | C$_2$H$_5$ | OCH$_3$ | 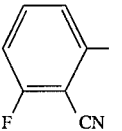 | m.p.: 147° C. |
| 24 | NH | C$_2$H$_5$ | OCH$_3$ | 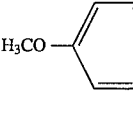 | m.p.: 144° C. |
| 25 | NH | C$_2$H$_5$ | OCH$_3$ | 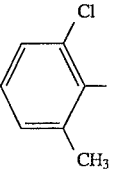 | m.p.: 164° C. |
| 26 | NH | C$_2$H$_5$ | OCH$_3$ | 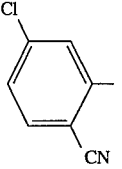 | m.p.: 160° C. |
| 27 | NH | C$_2$H$_5$ | OCH$_3$ | 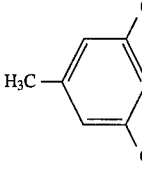 | m.p.: 183° C. |
| 28 | NH | C$_2$H$_5$ | OCH$_3$ | 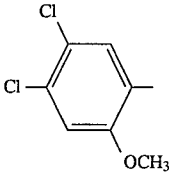 | m.p.: 157° C. |

TABLE 2-continued
Preparation examples of the compounds of the formula (I)
| Ex. No. | Q | R$^1$ | R$^2$ | R$^3$ | Physical data |
|---|---|---|---|---|---|
| 29 | NH | C$_2$H$_5$ | OCH$_3$ | 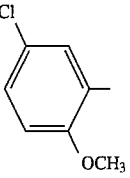 | m.p.: 156° C. |
| 30 | NH | CH$_3$ | OC$_2$H$_5$ | 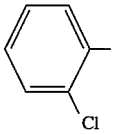 | m.p.: 160° C. |
| 31 | NH | CH$_3$ | OC$_2$H$_5$ | 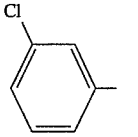 | m.p.: 130° C. |
| 32 | NH | CH$_3$ | OC$_2$H$_5$ | 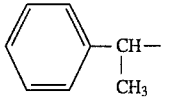 | m.p.: 160° C. |
| 33 | NH | CH$_3$ | OC$_2$H$_5$ | 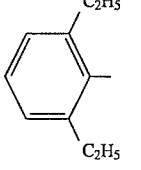 | m.p.: 149° C. |
| 34 | NH | CH$_3$ | OC$_2$H$_5$ | 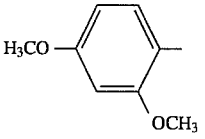 | m.p.: 131° C. |
| 35 | NH | CH$_3$ | OC$_2$H$_5$ | 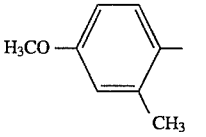 | m.p.: 151° C. |
| 36 | NH | CH$_3$ | OC$_2$H$_5$ | 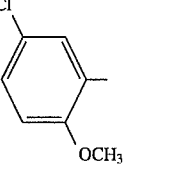 | m.p.: 155° C. |
| 37 | NH | CH$_3$ | OC$_2$H$_5$ | 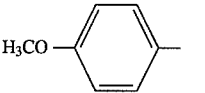 | m.p.: 163° C. |
| 38 | NH | CH$_3$ | OC$_2$H$_5$ | 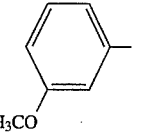 | m.p.: 148° C. |

TABLE 2-continued
Preparation examples of the compounds of the formula (I)
| Ex. No. | Q | R¹ | R² | R³ | Physical data |
|---|---|---|---|---|---|
| 39 | NH | $CH_3$ | $OC_2H_5$ | 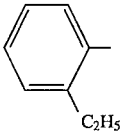 | m.p.: 145° C. |
| 40 | NH | $CH_3$ | $OC_2H_5$ | 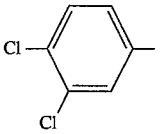 | m.p.: 171° C. |
| 41 | NH | $CH_3$ | $OC_2H_5$ | 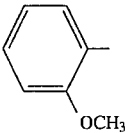 | m.p.: 120° C. |
| 42 | NH | $CH_3$ | $OC_2H_5$ | 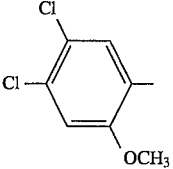 | m.p.: 165° C. |
| 43 | NH | $CH_3$ | $OC_2H_5$ | 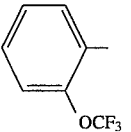 | m.p.: 129° C. |
| 44 | NH | $CH_3$ | $OC_2H_5$ | 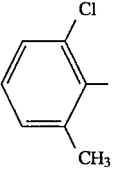 | m.p.: 170° C. |
| 45 | NH | $CH_3$ | $OC_2H_5$ | 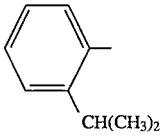 | m.p.: 139° C. |
| 46 | NH | $CH_3$ | $OC_2H_5$ | 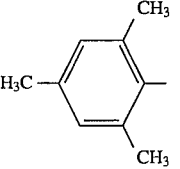 | m.p.: 184° C. |
| 47 | NH | $CH_3$ | $OC_2H_5$ | 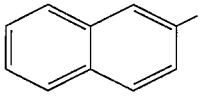 | m.p.: 158° C. |
| 48 | NH | $CH_3$ | $OC_2H_5$ | 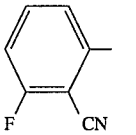 | m.p.: 158° C. |

TABLE 2-continued

Preparation examples of the compounds of the formula (I)

| Ex. No. | Q | R¹ | R² | R³ | Physical data |
|---|---|---|---|---|---|
| 49 | NH | $CH_3$ | $OC_2H_5$ | 2-SCH₃-phenyl | m.p.: 153° C. |
| 50 | NH | $CH_3$ | $OC_2H_5$ | 2,6-di-Cl-phenyl | m.p.: 160° C. |
| 51 | NH | $CH_3$ | $OC_2H_5$ | 2-NO₂-6-CH₃-phenyl | m.p.: 144° C. |
| 52 | NH | $CH_3$ | $OC_2H_5$ | 2-CN-phenyl | m.p.: 152° C. |
| 53 | NH | $CH_3$ | $OC_2H_5$ | 2-CF₃-phenyl | m.p.: 127° C. |
| 54 | NH | $CH_3$ | $OC_2H_5$ | 2-CN-6-Cl-phenyl | m.p.: 170° C. |
| 55 | NH | $CH_3$ | $OC_2H_5$ | 4-Cl-2-CF₃-phenyl | m.p.: 132° C. |
| 56 | NH | $CH_3$ | $OC_2H_5$ | 3-CH₃-phenyl | m.p.: 143° C. |
| 57 | NH | $CH_3$ | $OC_2H_5$ | 2-C(CH₃)₃-phenyl | m.p.: 152° C. |
| 58 | NH | $CH_3$ | $OC_2H_5$ | 2-Cl-6-C₂H₅-phenyl | m.p.: 170° C. |

TABLE 2-continued

Preparation examples of the compounds of the formula (I)

| Ex. No. | Q | R¹ | R² | R³ | Physical data |
|---|---|---|---|---|---|
| 59 | NH | $CH_3$ | $OC_2H_5$ | 2-($OSO_2C_6H_5$)phenyl | m.p.: 148° C. |
| 60 | NH | $CH_3$ | $OC_2H_5$ | 2-($SCH_2CH_2COOCH_3$)phenyl | $^1$H NMR ($CDCl_3$, δ): 2.52–2.58; 3.15; 3.70 ppm |
| 61 | NH | $CH_3$ | $OC_2H_5$ | 2-($SCH(CH_3)_2$)phenyl | m.p.: 94° C. |
| 62 | NH | $CH_3$ | $OC_2H_5$ | 2-F-phenyl | m.p.: 163° C. |
| 63 | NH | $CH_3$ | $OC_2H_5$ | 2-($SCH_2CH_2CN$)phenyl | m.p.: 124° C. |
| 64 | NH | $CH_3$ | $OC_2H_5$ | 2-($COCH_3$)phenyl | m.p.: 138° C. |
| 65 | $NCH_3$ | $CH_3$ | $OC_2H_5$ | 2-($OCH_3$)phenyl | m.p.: 149° C. |
| 66 | NH | $C_2H_5$ | $OCH_3$ | 1-($C_2H_5$)-5,6,7,8-tetrahydronaphthalen-2-yl | m.p.: 182° C. |
| 67 | NH | $C_2H_5$ | $OCH_3$ | 1-($OC_2H_5$)-5,6,7,8-tetrahydronaphthalen-2-yl | m.p.: 172° C. |
| 68 | NH | $C_2H_5$ | $OCH_3$ | 1,3-dichloronaphthalen-4-yl | m.p.: 167° C. |

TABLE 2-continued

Preparation examples of the compounds of the formula (I)

| Ex. No. | Q | R¹ | R² | R³ | Physical data |
|---|---|---|---|---|---|
| 69 | NH | $C_2H_5$ | $OCH_3$ | 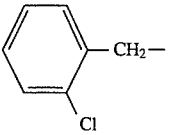 2-Cl-C₆H₄-CH₂— | m.p.: 140° C. |
| 70 | | $C_2H_5$ | $OCH_3$ | 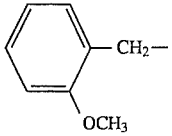 2-OCH₃-C₆H₄-CH₂— | m.p.: 130° C. |
| 71 | NH | $C_2H_5$ | $OCH_3$ | 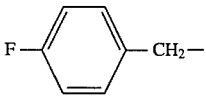 4-F-C₆H₄-CH₂— | m.p.: 167° C. |
| 72 | NH | $C_2H_5$ | $OCH_3$ | 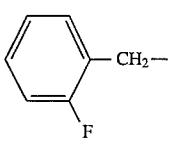 2-F-C₆H₄-CH₂— | m.p.: 145° C. |
| 73 | —O—NH— | $C_2H_5$ | $OCH_3$ | 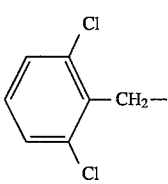 2,6-Cl₂-C₆H₃-CH₂— | m.p.: 165° C. |
| 74 | NH | $C_2H_5$ | $OCH_3$ | 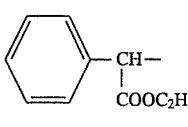 C₆H₅-CH(COOC₂H₅)— | m.p.: 100° C. |
| 75 | NH | $C_2H_5$ | $OCH_3$ | 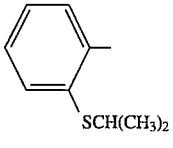 2-SCH(CH₃)₂-C₆H₄— | ¹H NMR (CDCl₃, δ): 1.23–1.25; 3.60–3.70; 4,08 ppm |
| 76 | NH | $C_2H_5$ | $OCH_3$ | 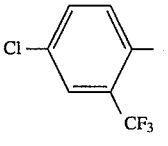 4-Cl-2-CF₃-C₆H₃— | m.p.: 122° C. |
| 77 | NH | $C_2H_5$ | $OCH_3$ | 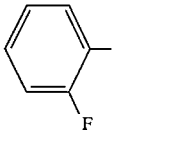 2-F-C₆H₄— | m.p.: 148° C. |
| 78 | NCH₃ | $C_2H_5$ | $OCH_3$ | 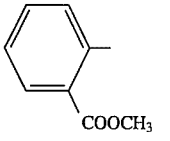 2-COOCH₃-C₆H₄— | ¹H NMR (CDCl₃, δ): 3.58; 3.92; 4.13 ppm |
| 79 | NH | $C_2H_5$ | $OCH_3$ | 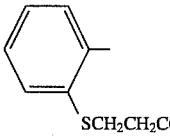 2-SCH₂CH₂COOCH₃-C₆H₄— | ¹H NMR (CDCl₃, δ): 2.50–2.60; 3.67; 4.05 ppm |

TABLE 2-continued

Preparation examples of the compounds of the formula (I)

| Ex. No. | Q | R¹ | R² | R³ | Physical data |
|---|---|---|---|---|---|
| 80 | NH | $C_2H_5$ | $OCH_3$ | 2-($SCH_2CH_2CN$)-phenyl | m.p.: 118° C. |
| 81 | NH | $C_2H_5$ | $OCH_3$ | 2-($C(CH_3)_3$)-phenyl | m.p.: 145° C. |
| 82 | $NCH_3$ | $C_2H_5$ | $OCH_3$ | 2,4-dichlorophenyl | m.p.: 130° C. |
| 83 | NH | $CH_3$ | $CH_3$ | 2-($OCH_3$)-phenyl | m.p.: 137° C. |
| 84 | NH | $-N=C(CH_3)(C_4H_9\text{-}i)$ | $N(CH_3)_2$ | 2-($OCH_3$)-phenyl | m.p.: 119° C. |
| 85 | NH | $C_2H_5$ | $OCH_3$ | 2-($CF_3$)-cyclohexyl (H) | m.p.: 152° C. |
| 86 | NH | $C_2H_5$ | $OCH_3$ | 2-($C_4H_9$-s)-cyclohexyl (H) | ¹H NMR (CDCl₃, δ): 3.63–3.70; 4.12 ppm |
| 87 | NH | $-N=C(CH_3)(C_4H_9\text{-}i)$ | $N(CH_3)_2$ | 2-($COOC_2H_5$)-phenyl | m.p.: 140° C. |
| 88 | NH | $C_2H_5$ | $OCH_3$ | 2-COOH-3-F-phenyl | m.p.: 169° C. |
| 89 | NH | $C_2H_5$ | $OCH_3$ | 2-($OCHF_2$)-phenyl | ¹H NMR (CDCl₃, δ): 3.60–3.67; 3.70–3.77; 4.10 ppm |

TABLE 2-continued

Preparation examples of the compounds of the formula (I)

| Ex. No. | Q | R¹ | R² | R³ | Physical data |
|---|---|---|---|---|---|
| 90 | NH | $C_2H_5$ | $OCH_3$ | 2-methoxyphenyl-CH₂CH₂— | m.p.: 120° C. |
| 91 | NH | $C_2H_5$ | $OCH_3$ | 2-(COCH₃)phenyl- | m.p.: 158° C. |
| 92 | NH | $C_2H_5$ | $OCH_3$ | 2-CN-4-CF₃-phenyl- | m.p.: 160° C. |
| 93 | NH | $C_2H_5$ | $OCH_3$ | 1-methylcyclohexyl- (with H) | m.p.: 127° C. |
| 94 | NH | $C_2H_5$ | $OCH_3$ | 4-($F_3CS$)phenyl- | m.p.: 150° C. |
| 95 | NH | $C_2H_5$ | $OCH_3$ | 4-($F_3CO$)phenyl- | m.p.: 125° C. |
| 96 | NH | $C_2H_5$ | $OCH_3$ | 1-methylcyclopentyl- | m.p.: 121° C. |
| 97 | NH | $C_2H_5$ | $OCH_3$ | 3-$CF_3$-4-F-phenyl- | m.p.: 150° C. |
| 98 | NH | $C_2H_5$ | $OCH_3$ | 3-$CF_3$-4-Br-phenyl- | m.p.: 151° C. |
| 99 | NH | $C_2H_5$ | $OCH_3$ | cyclopropyl- | m.p.: 133° C. |
| 100 | NH | $C_2H_5$ | $OCH_3$ | 4-($H_3C-CO$)phenyl- | m.p.: 165° C. |

TABLE 2-continued

Preparation examples of the compounds of the formula (I)

| Ex. No. | Q | R¹ | R² | R³ | Physical data |
|---|---|---|---|---|---|
| 101 | NH | $CH_3$ | $n\text{-}C_3H_7$ | 2-($SCH(CH_3)_2$)-phenyl | $^1$H NMR (CDCl$_3$, δ): 2.50–2.55; 3.25; 4.15–4.20 ppm |
| 102 | NH | $CH_3$ | $n\text{-}C_3H_7$ | 2-($COOC_2H_5$)-phenyl | m.p.: 180° C. |
| 103 | NH | $CH_3$ | $n\text{-}C_3H_7$ | 2-($OC_2H_5$)-phenyl | m.p.: 111° C. |
| 104 | NH | $C_2H_5$ | $OCH_3$ | phenyl-CH(CN)- | m.p.: 170° C. |
| 105 | NH | $C_2H_5$ | $OCH_3$ | 2,6-dichloro-4-(CF$_3$)-phenyl | m.p.: 135° C. |
| 106 | NH | $CH_3$ | $OC_6H_5$ | 2-($OCH_3$)-phenyl | m.p.: 146° C. |
| 107 | NH | $C_2H_5$ | $OCH_3$ | 4-(4-chlorophenoxy)-phenyl | m.p.: 158° C. |
| 108 | NH | $C_2H_5$ | $OCH_3$ | 2,5-difluoro-phenyl | m.p.: 148° C. |
| 109 | NH | $C_2H_5$ | $OCH_3$ | 3,5-bis(CF$_3$)-phenyl | m.p.: 140° C. |
| 110 | NH | $C_2H_5$ | $OCH_3$ | 4-isopropyl-phenyl | m.p.: 170° C. |
| 111 | NH | $CH_3$ | $OC_2H_5$ | phenyl | m.p.: 162° C. |

TABLE 2-continued

Preparation examples of the compounds of the formula (I)

| Ex. No. | Q | R¹ | R² | R³ | Physical data |
|---|---|---|---|---|---|
| 112 | −N−CH₂−C(=O)−OC₂H₅ | C₂H₅ | OCH₃ | 2,6-di(C₂H₅)-phenyl | m.p.: 103° C. |
| 113 | NH | C₂H₅ | OCH₃ | 4-OCH₃-3-(COOC₂H₅)-phenyl | m.p.: 125° C. |
| 114 | NH | C₂H₅ | OCH₃ | 4-OC₂H₅-3-NO₂-phenyl | m.p.: 150° C. |
| 115 | −N−C(=O)−OC₂H₅ | C₂H₅ | OCH₃ | 2-OCH₃-phenyl | m.p.: 135° C. |
| 116 | −N−CH₂−C(=O)−OC₂H₅ | C₂H₅ | OCH₃ | 2-CH₃-6-C₂H₅-phenyl | ¹H NMR (CDCl₃, δ): 2.5; 3.60–3.70; 4.10 ppm |
| 117 | NH | C₂H₅ | OCH₃ | 4-s-C₄H₉-phenyl | m.p.: 140° C. |
| 118 | NH | C₂H₅ | OCH₃ | 3-(F₉C₄O₂SO)-phenyl | ¹H NMR (CDCl₃, δ): 3.60–3.67; 4.05; 8.30 ppm |
| 119 | NH | C₂H₅ | OCH₃ | 2,6-dichloro-4-phenoxy-phenyl | m.p.: 165° C. |
| 120 | NH | C₂H₅ | OCH₃ | 3-NO₂-4-phenoxy-phenyl | m.p.: 161° C. |

TABLE 2-continued
Preparation examples of the compounds of the formula (I)
| Ex. No. | Q | R¹ | R² | R³ | Physical data |
|---|---|---|---|---|---|
| 121 | NH | C₂H₅ | OCH₃ | 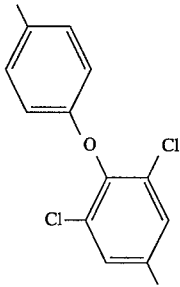 | m.p.: 172° C. |
| 122 | NH | C₂H₅ | OCH₃ | 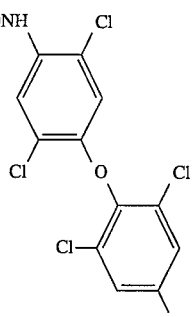 | m.p.: 190° C. |
| 123 | NH | C₂H₅ | OCH₃ | 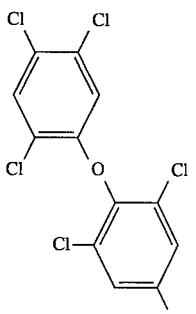 | m.p.: 185° C. |
| 124 | NH | C₂H₅ | OCH₃ | 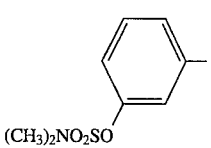 | m.p.: 147° C. |
| 125 | NH | C₂H₅ | OCH₃ | 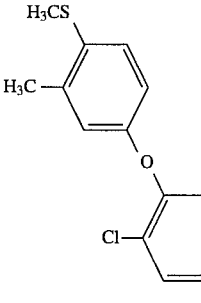 | m.p.: 160° C. |

TABLE 2-continued
Preparation examples of the compounds of the formula (I)
| Ex. No. | Q | R¹ | R² | R³ | Physical data |
|---|---|---|---|---|---|
| 126 | NH | $C_2H_5$ | $OCH_3$ | 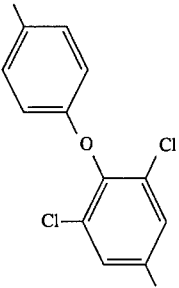 | m.p.: 193° C. |
| 127 | NH | $C_2H_5$ | $OCH_3$ | 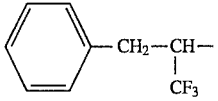 | m.p.: 190° C. |
| 128 | NH | $C_2H_5$ | $OCH_3$ | 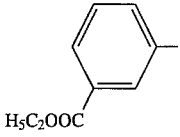 | m.p.: 154° C. |
| 129 | NH | $C_2H_5$ | $OCH_3$ | 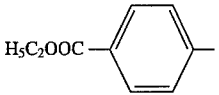 | m.p.: 168° C. |
| 130 | NH | $C_2H_5$ | $OCH_3$ | 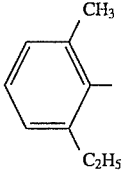 | m.p.: 154° C. |
| 131 | NH | $C_2H_5$ | $OCH_3$ | 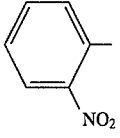 | m.p.: 135° C. |
| 132 | NH | $C_2H_5$ | $OCH_3$ | 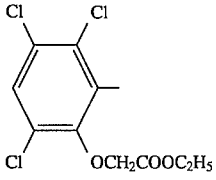 | m.p.: 193° C. |
| 133 | NH | $CH_3$ | $OC_3H_7\text{-}i$ | 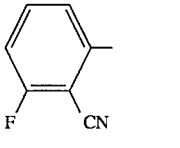 | m.p.: 138° C. |
| 134 | NH | $CH_3$ | $OC_3H_7\text{-}i$ | 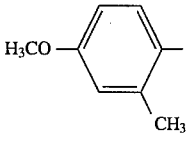 | m.p.: 138° C. |

TABLE 2-continued

Preparation examples of the compounds of the formula (I)

| Ex. No. | Q | R¹ | R² | R³ | Physical data |
|---|---|---|---|---|---|
| 135 | NH | $CH_3$ | $OC_3H_7$-i | 2-methoxyphenyl | m.p.: 144° C. |
| 136 | NH | $CH_3$ | $OC_3H_7$-i | 2-($COOC_2H_5$)phenyl | m.p.: 130° C. |
| 137 | NH | $CH_3$ | $OC_3H_7$-i | 2-fluorophenyl | m.p.: 137° C. |
| 138 | NH | $CH_3$ | $OC_3H_7$-i | 2,5-difluorophenyl | m.p.: 146° C. |
| 139 | NH | $CH_3$ | $OC_3H_7$-i | 2-($OCF_3$)phenyl | m.p.: 141° C. |
| 140 | NH | $CH_3$ | $OC_3H_7$-i | 2-ethylphenyl | m.p.: 128° C. |
| 141 | NH | $CH_3$ | $OC_3H_7$-i | 2-($CF_3$)phenyl | m.p.: 135° C. |
| 142 | NH | $CH_3$ | $OC_3H_7$-i | 3,5-bis($H_3COOC$)phenyl | m.p.: 165° C. |
| 143 | NH | $CH_3$ | $OC_3H_7$-i | 2-methyl-6-nitrophenyl | m.p.: 138° C. |
| 144 | NH | $CH_3$ | $OC_3H_7$-i | 2-nitrophenyl | m.p.: 120° C. |

TABLE 2-continued

Preparation examples of the compounds of the formula (I)

| Ex. No. | Q | R¹ | R² | R³ | Physical data |
|---|---|---|---|---|---|
| 145 | NH | $CH_3$ | $OC_3H_7$-i | 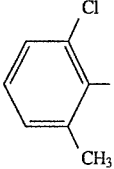 2-Cl, 6-$CH_3$-phenyl | m.p.: 138° C. |
| 146 | NH | $CH_3$ | $OC_3H_7$-i | 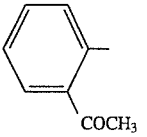 2-$COCH_3$-phenyl | m.p.: 150° C. |
| 147 | NH | $CH_3$ | $OC_3H_7$-i | 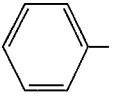 phenyl | m.p.: 150° C. |
| 148 | NH | $C_2H_5$ | $OCH_3$ | 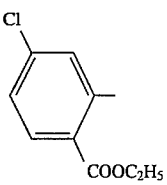 4-Cl, 2-$COOC_2H_5$-phenyl | m.p.: 141° C. |
| 149 | NH | $C_2H_5$ | $OCH_3$ | 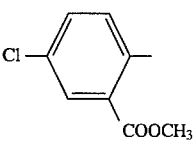 5-Cl, 2-$COOCH_3$-phenyl | m.p.: 150° C. |
| 150 | NH | $C_2H_5$ | $OCH_3$ | 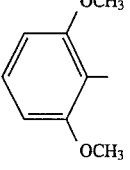 2,6-di-$OCH_3$-phenyl | m.p.: 170° C. |
| 151 | NH | $C_2H_5$ | $OCH_3$ | 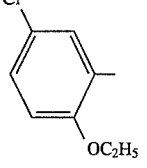 4-Cl, 2-$OC_2H_5$-phenyl | m.p.: 143° C. |
| 152 | NH | $C_2H_5$ | $OCH_3$ | 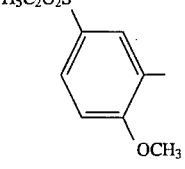 3-$SO_2C_2H_5$, 4-$OCH_3$-phenyl | m.p.: 118° C. |
| 153 | NH | $C_2H_5$ | $OCH_3$ | 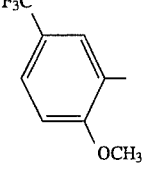 3-$CF_3$, 4-$OCH_3$-phenyl | m.p.: 142° C. |

TABLE 2-continued
Preparation examples of the compounds of the formula (I)
| Ex. No. | Q | R¹ | R² | R³ | Physical data |
|---|---|---|---|---|---|
| 154 | NH | $C_2H_5$ | $OCH_3$ | 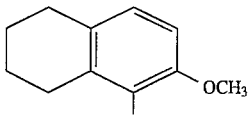 | m.p.: 192° C. |
| 155 | NH | $C_2H_5$ | $OCH_3$ | 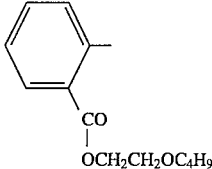 | m.p.: 80° C. |
| 156 | NH | $C_2H_5$ | $OCH_3$ | 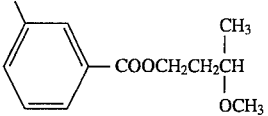 | m.p.: 107° C. |
| 157 | NH | $C_2H_5$ | $OCH_3$ | 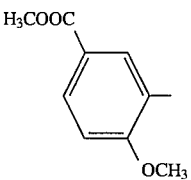 | m.p.: 159° C. |
| 158 | NH | $C_2H_5$ | $OCH_3$ | 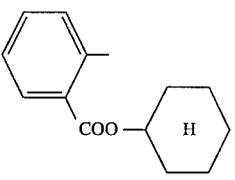 | m.p.: 129° C. |
| 159 | NH | $C_2H_5$ | $OCH_3$ | 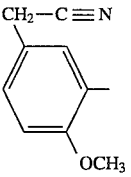 | m.p.: 137° C. |
| 160 | NH | $C_2H_5$ | $OCH_3$ | 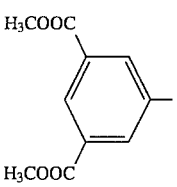 | m.p.: 183° C. |
| 161 | NH | $C_2H_5$ | $OCH_3$ |  | m.p.: 158° C. |
| 162 | NH | $C_2H_5$ | $OCH_3$ | 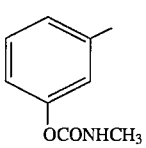 | m.p.: 155° C. |

TABLE 2-continued

Preparation examples of the compounds of the formula (I)

| Ex. No. | Q | R¹ | R² | R³ | Physical data |
|---|---|---|---|---|---|
| 163 | NH | CH₃ |  | 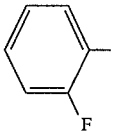 | m.p.: 140° C. |
| 164 | NH | CH₃ |  | 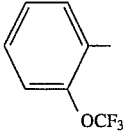 | m.p.: 129° C. |
| 165 | NCH₃ | OCH₃ | OCH₃ | CH₃ | m.p.: 154° C. |
| 166 | NCH₃ | CH₃ | n-C₃H₇ | —SO₂CH₃ | m.p.: 93° C. |
| 167 | NCH₃ | CH₃ | C₂H₅ | —SO₂CH₃ | m.p.: 124° C. |
| 168 | NCH₃ | CH₃ | SCH₃ | —SO₂CH₃ | m.p.: 160° C. |
| 169 | NCH₃ | CH₃ | SC₂H₅ | —SO₂CH₃ | m.p.: 116° C. |
| 170 | NCH₃ | OCH₃ | C₂H₅ | —SO₂CH₃ | m.p.: 103° C. |
| 171 | NCH₃ |  | Cl | —SO₂CH₃ | m.p.: 121° C. |
| 172 | O | CH₃ | OC₂H₅ | 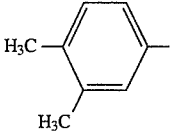 | m.p.: 135° C. |
| 173 | O | C₂H₅ | OCH₃ | 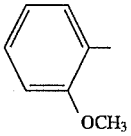 | ¹H NMR (CDCl₃, δ): 3.65–3.72; 3.85; 4.15 ppm |
| 174 | O |  | SCH₃ | 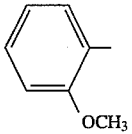 | m.p.: 110° C. |
| 175 | O |  | SC₂H₅ | 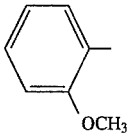 | m.p.: 100° C. |
| 176 | O | CH₃ | C₂H₅ | 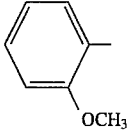 | m.p.: 132° C. |
| 177 | O | CH₃ | n-C₃H₇ | 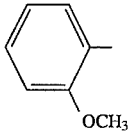 | m.p.: 107° C. |
| 178 | O |  | Br | 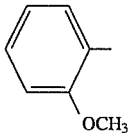 | m.p.: 137° C. |

TABLE 2-continued

Preparation examples of the compounds of the formula (I)

| Ex. No. | Q | R¹ | R² | R³ | Physical data |
|---|---|---|---|---|---|
| 179 | O | $CH_3$ | $SCH_3$ | 2-($OC_2H_5$)phenyl | m.p.: 116° C. |
| 180 | O | $CH_3$ | $SC_2H_5$ | 2-($OC_2H_5$)phenyl | m.p.: 103° C. |
| 181 | O | cyclopropyl | $C_2H_5$ | 2-($OC_2H_5$)phenyl | m.p.: 119° C. |
| 182 | O | cyclopropyl | $n-C_3H_7$ | 2-($OC_2H_5$)phenyl | m.p.: 94° C. |
| 183 | O | cyclopropyl | Cl | 2-($OC_2H_5$)phenyl | m.p.: 121° C. |
| 184 | O | $OCH_3$ | $C_2H_5$ | 2-($COOCH_3$)phenyl | m.p.: 96° C. |
| 185 | O | cyclopropyl | Cl | 2-($COOCH_3$)phenyl | m.p.: 128° C. |
| 186 | O | $CH_3$ | $C_2H_5$ | 2-Cl-phenyl | m.p.: 91° C. |
| 187 | O | $CH_3$ | $SCH_3$ | 2-Cl-phenyl | m.p.: 139° C. |
| 188 | O | $CH_3$ | $SC_2H_5$ | 2-Cl-phenyl | m.p.: 97° C. |

TABLE 2-continued

Preparation examples of the compounds of the formula (I)

| Ex. No. | Q | R¹ | R² | R³ | Physical data |
|---|---|---|---|---|---|
| 189 | O |  | Br | 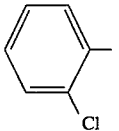 (2-Cl-phenyl) | m.p.: 120° C. |
| 190 | O | CH₃ | SCH₃ | 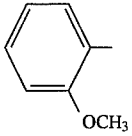 (2-OCH₃-phenyl) | m.p.: 129° C. |
| 191 | O | CH₃ | SC₂H₅ | 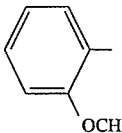 (2-OCH₃-phenyl) | m.p.: 146° C. |
| 192 | O |  | C₂H₅ | 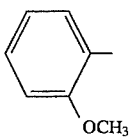 (2-OCH₃-phenyl) | m.p.: 108° C. |
| 193 | O |  | n-C₃H₇ | 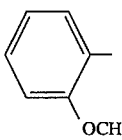 (2-OCH₃-phenyl) | m.p.: 118° C. |
| 194 | O |  | n-C₃H₇ | 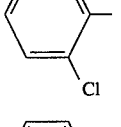 (2-Cl-phenyl) | m.p.: 99° C. |
| 195 | O | OCH₃ | C₂H₅ | 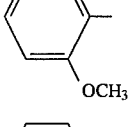 (2-OCH₃-phenyl) | m.p.: 120° C. |
| 196 | O | OCH₃ | n-C₃H₇ | 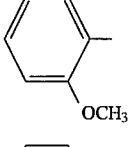 (2-OCH₃-phenyl) | m.p.: 105° C. |
| 197 | NH | CH₃ | OCH₃ | 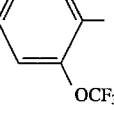 (2-OCF₃-phenyl) | m.p.: 132° C. |
| 198 | —N—<br>\|<br>CH₂CN | C₂H₅ | OCH₃ | 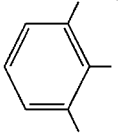 (2,6-di-C₂H₅-phenyl) | m.p.: 157° C. |

TABLE 2-continued

Preparation examples of the compounds of the formula (I)

| Ex. No. | Q | R¹ | R² | R³ | Physical data |
|---|---|---|---|---|---|
| 199 | NH | $CH_3$ | $OC_3H_7$-i | 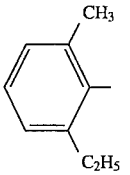 2-$CH_3$, 6-$C_2H_5$-phenyl | m.p.: 139° C. |
| 200 | NH | $C_2H_5$ | $OCH_3$ | 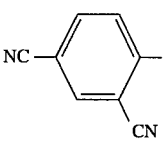 2,4-di-CN-phenyl | m.p.: 140° C. |
| 201 | NH | $C_2H_5$ | $OCH_3$ | 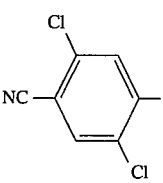 2,5-di-Cl-4-CN-phenyl | m.p.: 178° C. |
| 202 | NH | $C_2H_5$ | $OCH_3$ | 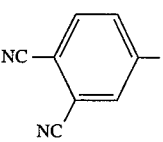 2,3-di-CN-phenyl | m.p.: 190° C. |
| 203 | NH | $CH_3$ | $N(CH_3)_2$ | 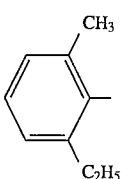 2-$CH_3$, 6-$C_2H_5$-phenyl | m.p.: 160° C. |
| 204 | NH | $CH_3$ | $N(CH_3)_2$ | 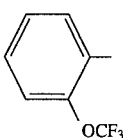 2-$OCF_3$-phenyl | m.p.: 161° C. |
| 205 | NH | $CH_3$ | $N(CH_3)_2$ | 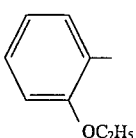 2-$OC_2H_5$-phenyl | m.p.: 151° C. |
| 206 | NH | $CH_3$ | $N(CH_3)_2$ | 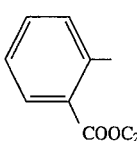 2-$COOC_2H_5$-phenyl | m.p.: 140° C. |
| 207 | NH | $CH_3$ | $N(CH_3)_2$ | 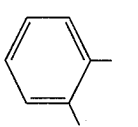 2-$COCH_3$-phenyl | m.p.: 135° C. |
| 208 | NH | $CH_3$ | $N(CH_3)_2$ | 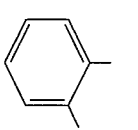 2-$SCH_3$-phenyl | m.p.: 124° C. |

TABLE 2-continued

Preparation examples of the compounds of the formula (I)

| Ex. No. | Q | R¹ | R² | R³ | Physical data |
|---|---|---|---|---|---|
| 209 | NH | $CH_3$ | $N(CH_3)_2$ | 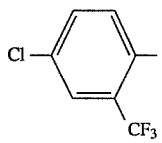 4-Cl, 2-CF₃-phenyl | m.p.: 131° C. |
| 210 | NH | $CH_3$ | $N(CH_3)_2$ | 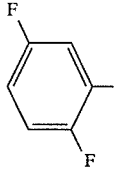 2,5-difluorophenyl | m.p.: 172° C. |
| 211 | NH | $CH_3$ | $N(CH_3)_2$ | 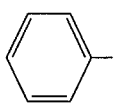 phenyl | m.p.: 140° C. |
| 212 | NH | $CH_3$ | $N(CH_3)_2$ | 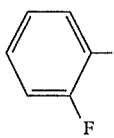 2-F-phenyl | m.p.: 161° C. |
| 213 | NH | $C_2H_5$ | $OCH_3$ | 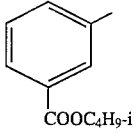 3-COOC₄H₉-i-phenyl | m.p.: 130° C. |
| 214 | NH | $C_2H_5$ | $OCH_3$ | 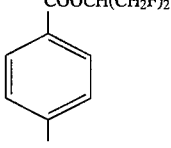 4-COOCH(CH₂F)₂-phenyl | ¹H NMR (CDCl₃, δ): 4.05; 4.62–4.64; 4.80–4.82 ppm |
| 215 | NH | $C_2H_5$ | $OCH_3$ | 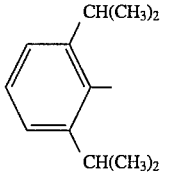 2,6-di-iPr-phenyl | m.p.: 174° C. |
| 216 | NH | $C_2H_5$ | $OCH_3$ | 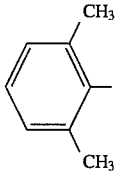 2,6-dimethylphenyl | m.p.: 169° C. |
| 217 | NH | $CH_3$ | $N(CH_3)_2$ | 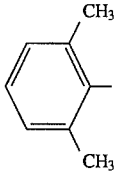 2,6-dimethylphenyl | m.p.: 156° C. |

TABLE 2-continued

Preparation examples of the compounds of the formula (I)

| Ex. No. | Q | R¹ | R² | R³ | Physical data |
|---|---|---|---|---|---|
| 218 | NH | $CH_3$ | $-CH_2-SCH_3$ | 2-($COOC_2H_5$)phenyl | m.p.: 106° C. |
| 219 | NH | $CH_3$ | $-CH_2-SCH_3$ | 2-$CH_3$,4-$C_2H_5$-phenyl | m.p.: 148° C. |
| 220 | NH | $CH_3$ | $OCH_3$ | 2-($OCH_3$)phenyl | m.p.: 149° C. |
| 221 | NH | $CH_3$ | $SC_2H_5$ | 2-($OCH_3$)phenyl | m.p.: 112° C. |
| 222 | NH | $CH_3$ | $OC_3H_7$-i | 2-Cl,4-CN-phenyl | m.p.: 131° C. |
| 223 | NH | $CH_3$ | $OC_3H_7$-i | 2,4-di($CH(CH_3)_2$)phenyl | m.p.: 156° C. |
| 224 | NH | $CH_3$ | cyclopropyl | 2-($OCH_3$)phenyl | m.p.: 144° C. |
| 225 | NH | $CH_3$ | cyclopropyl | 2-($COOCH_3$)phenyl | m.p.: 157° C. |
| 226 | $-N(CH_3)-$ | $CH_3$ | $OC_3H_7$-i | 2-($COOCH_3$)phenyl | m.p.: 136° C. |
| 227 | NH | $CH_3$ | $OC_3H_7$-i | 3-$CH_3$,2-$OC_2H_5$-5,6,7,8-tetrahydronaphthyl | m.p.: 161° C. |

TABLE 2-continued

Preparation examples of the compounds of the formula (I)

| Ex. No. | Q | R¹ | R² | R³ | Physical data |
|---|---|---|---|---|---|
| 228 | NH | CH₃ | OC₃H₇-i | 4-(COCH₃)-C₆H₄ | m.p.: 149° C. |
| 229 | NH | CH₃ | OC₃H₇-i | 4-(COOC₂H₅)-C₆H₄ | m.p.: 138° C. |
| 230 | NH | CH₃ | OC₃H₇-i | 4-(COOC₂H₅)-C₆H₄ | m.p.: 149° C. |
| 231 | NH | CH₃ | OC₃H₇-i | 2-(OC₂H₅)-C₆H₄ | m.p.: 115° C. |
| 232 | NH | CH₃ | OC₃H₇-i | 2-(SCH₃)-C₆H₄ | m.p.: 121° C. |
| 233 | NH | CH₃ | OC₃H₇-i | 2-Cl-C₆H₄ | m.p.: 123° C. |
| 234 | NH | CH₃ | OC₃H₇-i | 2-(S—CH(CH₃)₂)-C₆H₄ | ¹H NMR (CDCl₃, δ): 1.2–1.25; 3.15; 3.15–3.25 ppm |
| 235 | NH | CH₃ | OC₃H₇-i | [2-methyl-5-CF₃-phenyl]-C(=O)-[2-Cl-5-CF₃-phenyl] | m.p.: 130° C. |
| 236 | NH | CH₃ | OC₃H₇-i | 2-(COO—CH₂-cyclohexyl)-C₆H₄ | m.p.: 131° C. |

TABLE 2-continued

Preparation examples of the compounds of the formula (I)

| Ex. No. | Q | R¹ | R² | R³ | Physical data |
|---|---|---|---|---|---|
| 237 | —N(CH₃)— | CH₃ | OC₃H₇-i | 2-OCH₃-phenyl | m.p.: 121° C. |
| 238 | NH | CH₃ | OC₃H₇-i | 2-CH(CH₃)₂-phenyl | m.p.: 139° C. |
| 239 | NH | CH₃ | OC₃H₇-i | 2-COOCH₃-phenyl | m.p.: 145° C. |
| 240 | NH | CH₃ | cyclopropyl | 2-COCH₃-phenyl | m.p.: 140° C. |
| 241 | NH | CH₃ | cyclopropyl | phenyl | m.p.: 146° C. |
| 242 | —N(COOC₂H₅)— | CH₃ | OC₃H₇-i | phenyl | m.p.: 156° C. |
| 243 | NH | CH₃ | OC₃H₇-i | 3-COOC₂H₅-5-NO₂-phenyl | m.p.: 141° C. |
| 244 | NH | CH₃ | i-C₃H₇ | 2-OCF₃-phenyl | m.p.: 148° C. |
| 245 | NH | CH₃ | i-C₃H₇ | 2-OC₂H₅-phenyl | m.p.: 127° C. |
| 246 | NH | CH₃ | i-C₃H₇ | 2-COOC₂H₅-phenyl | m.p.: 142° C. |
| 247 | NH | CH₃ | i-C₃H₇ | 2-OCH₃-phenyl | m.p.: 155° C. |

TABLE 2-continued

Preparation examples of the compounds of the formula (I)

| Ex. No. | Q | $R^1$ | $R^2$ | $R^3$ | Physical data |
|---------|----|-------|-------|-------|---------------|
| 248 | NH | $CH_3$ | $i\text{-}C_3H_7$ |  2-COCH$_3$-phenyl | m.p.: 148° C. |
| 249 | NH | $CH_3$ | $i\text{-}C_3H_7$ | 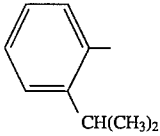 2-CH(CH$_3$)$_2$-phenyl | m.p.: 137° C. |
| 250 | NH | $CH_3$ | $i\text{-}C_3H_7$ | 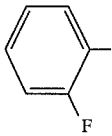 2-F-phenyl | m.p.: 144° C. |
| 251 | NH | $CH_3$ | $i\text{-}C_3H_7$ | 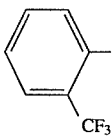 2-CF$_3$-phenyl | m.p.: 136° C. |
| 252 | NH | $CH_3$ | $i\text{-}C_3H_7$ | 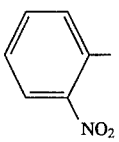 2-NO$_2$-phenyl | m.p.: 120° C. |
| 253 | NH | $CH_3$ | $O\text{-}C_3H_7\text{-}i$ | 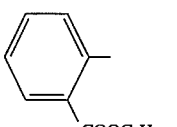 2-COOC$_3$H$_7$-n-phenyl | m.p.: 139° C. |
| 254 | NH | $CH_3$ | $i\text{-}C_3H_7$ | 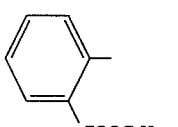 2-COOC$_3$H$_7$-n-phenyl | m.p.: 96° C. |
| 255 | NH | $CH_3$ | $O\text{-}C_3H_7\text{-}i$ | 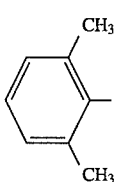 2,6-(CH$_3$)$_2$-phenyl | m.p.: 154° C. |
| 256 | NH | $CH_3$ | $O\text{-}C_2H_5$ | 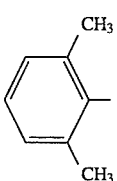 2,6-(CH$_3$)$_2$-phenyl | m.p.: 165° C. |
| 257 | NH | $CH_3$ | $O\text{-}C_2H_5$ | 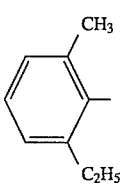 2-CH$_3$-6-C$_2$H$_5$-phenyl | m.p.: 164° C. |

TABLE 2-continued
Preparation examples of the compounds of the formula (I)
| Ex. No. | Q | R¹ | R² | R³ | Physical data |
|---|---|---|---|---|---|
| 258 | NH | CH₃ |  | 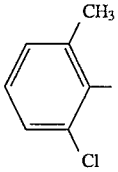 | m.p.: 155° C. |
| 259 | NH | CH₃ | i-C₃H₇ | 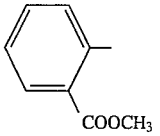 | m.p.: 165° C. |
| 260 | NH | CH₃ |  | 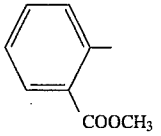 | m.p.: 167° C. |
| 261 | NH | CH₃ | OC₂H₅ | 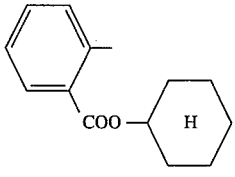 | m.p.: 130° C. |
| 262 | NH | CH₃ |  | 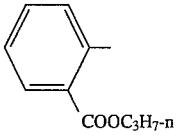 | m.p.: 139° C. |
| 263 | NH | CH₃ | O—C₃H₇-i | 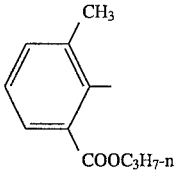 | m.p.: 109° C. |
| 264 | NH | CH₃ | OC₂H₅ | 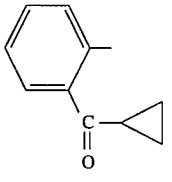 | m.p.: 157° C. |
| 265 | NH | CH₃ | C₃H₇-i | 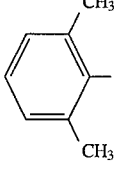 | m.p.: 145° C. |
| 266 | NH | CH₃ | OC₂H₅ | 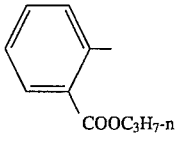 | m.p.: 135° C. |

TABLE 2-continued

Preparation examples of the compounds of the formula (I)

| Ex. No. | Q | R¹ | R² | R³ | Physical data |
|---|---|---|---|---|---|
| 267 | NH | $CH_3$ | $OC_2H_5$ | 2-($C(=O)C_6H_5$)-phenyl | m.p.: 124° C. |
| 268 | NH | $CH_3$ | $OC_2H_5$ | 2-($OCHF_2$)-phenyl | m.p.: 89° C. |
| 269 | NH | $CH_3$ | $OC_2H_5$ | 2,6-bis($CH(CH_3)_2$)-phenyl | m.p.: 164° C. |
| 270 | NH | $CH_3$ | $OCH_3$ | 2-(cyclopropyl-C(=O))-phenyl | m.p.: 157° C. |
| 271 | —N(CH$_3$)— | $CH_3$ | $OC_2H_5$ | $-SO_2CH_3$ | m.p.: 145° C. |
| 272 | NH | $CH_3$ | $OC_3H_7$-i | 2-(cyclopropyl-C(=O))-phenyl | m.p.: 164° C. |
| 273 | NH | $CH_3$ | $OC_2H_5$ | 2-($C(=O)C_6H_5$)-phenyl | m.p.: 136° C. |
| 274 | NH | $CH_3$ | $OC_2H_4-OC_2H_5$*⁾ | 2-($OCF_3$)-phenyl | m.p.: 101° C. |
| 275 | NH | $CH_3$ | $OC_2H_4-OC_2H_5$*⁾ | 2-($CF_3$)-phenyl | m.p.: 79° C. |
| 276 | NH | $CH_3$ | $OC_2H_4-OC_2H_5$*⁾ | 2-($OCH_3$)-phenyl | m.p.: 84° C. |

TABLE 2-continued

Preparation examples of the compounds of the formula (I)

| Ex. No. | Q | $R^1$ | $R^2$ | $R^3$ | Physical data |
|---|---|---|---|---|---|
| 277 | NH | $CH_3$ | $OC_2H_4-$<br>$OC_2H_5$*) | 2-($OC_2H_5$)-phenyl | m.p.: 123° C. |
| 278 | NH | $CH_3$ | $OC_2H_4-$<br>$OC_2H_5$*) | 2-($COOC_2H_5$)-phenyl | m.p.: 104° C. |
| 279 | NH | $CH_3$ | $OC_2H_4-$<br>$OC_2H_5$*) | phenyl | m.p.: 111° C. |
| 280 | NH | $CH_3$ | $OC_2H_4-$<br>$OC_2H_5$*) | 2-($COOCH_3$)-phenyl | m.p.: 121° C. |
| 281 | NH | $CH_3$ | $OC_2H_4-$<br>$OC_2H_5$*) | 2-$CH_3$,3-$C_2H_5$-phenyl | m.p.: 112° C. |
| 282 | NH | $CH_3$ | $OC_2H_4-$<br>$OC_2H_5$*) | 2,3-di-$CH_3$-phenyl | m.p.: 117° C. |
| 283 | NH | $CH_3$ | $OC_2H_4-$<br>$OC_2H_5$*) | 2,3-di-$C_2H_5$-phenyl | m.p.: 92° C. |
| 284 | NH | $CH_3$ | $OC_2H_4-$<br>$OCH_3$*) | 2-($OCF_3$)-phenyl | m.p.: 103° C. |
| 285 | NH | $CH_3$ | $OC_2H_4-$<br>$OCH_3$*) | 2-($CF_3$)-phenyl | m.p.: 106° C. |
| 286 | NH | $CH_3$ | $OC_2H_4-$<br>$OCH_3$*) | 2-($OCH_3$)-phenyl | m.p.: 105° C. |

TABLE 2-continued

Preparation examples of the compounds of the formula (I)

| Ex. No. | Q | R¹ | R² | R³ | Physical data |
|---|---|---|---|---|---|
| 287 | NH | $CH_3$ | $OC_2H_4-OCH_3$*) | phenyl-$OC_2H_5$ | m.p.: 115° C. |
| 288 | NH | $CH_3$ | $OC_2H_4-OCH_3$*) | phenyl-$COOC_2H_5$ | m.p.: 108° C. |
| 289 | NH | $CH_3$ | $OC_2H_4-OCH_3$*) | phenyl | m.p.: 126° C. |
| 290 | NH | $CH_3$ | $OC_2H_4-OCH_3$*) | phenyl-$COOCH_3$ | m.p.: 132° C. |
| 291 | NH | $CH_3$ | $OC_2H_4-OCH_3$*) | phenyl-$CH_3$, $C_2H_5$ | m.p.: 135° C. |
| 292 | NH | $CH_3$ | $OC_2H_4-OCH_3$*) | phenyl-$CH_3$, $CH_3$ | m.p.: 141° C. |
| 293 | NH | $CH_3$ | $OC_2H_4-OCH_3$*) | phenyl-$C_2H_5$, $C_2H_5$ | m.p.: 79° C. |
| 294 | NH | $CH_3$ | $OC_2H_4-OC_3H_7$-i*) | phenyl-$OCF_3$ | m.p.: 102° C. |
| 295 | NH | $CH_3$ | $OC_2H_4-OC_3H_7$-i*) | phenyl-$CF_3$ | m.p.: 115° C. |
| 296 | NH | $CH_3$ | $OC_2H_4-OC_3H_7$-i*) | phenyl-$OCH_3$ | m.p.: 68° C. |

TABLE 2-continued

Preparation examples of the compounds of the formula (I)

| Ex. No. | Q | R$^1$ | R$^2$ | R$^3$ | Physical data |
|---|---|---|---|---|---|
| 297 | NH | CH$_3$ | OC$_2$H$_4$—OC$_3$H$_7$-i*) | 2-OC$_2$H$_5$-phenyl | m.p.: 59° C. |
| 298 | NH | CH$_3$ | OC$_2$H$_4$—OC$_3$H$_7$-i*) | 2-COOC$_2$H$_5$-phenyl | m.p.: 71° C. |
| 299 | NH | CH$_3$ | OC$_2$H$_4$—OC$_3$H$_7$-i*) | phenyl | m.p.: 85° C. |
| 300 | NH | CH$_3$ | OC$_2$H$_4$—OC$_3$H$_7$-i*) | 2-COOCH$_3$-phenyl | m.p.: 91° C. |
| 301 | NH | CH$_3$ | OC$_2$H$_4$—OC$_3$H$_7$-i*) | 2-CH$_3$-4-C$_2$H$_5$-phenyl | m.p.: 114° C. |
| 302 | NH | CH$_3$ | OC$_2$H$_4$—OC$_3$H$_7$-i*) | 2,4-(CH$_3$)$_2$-phenyl | m.p.: 109° C. |
| 303 | NH | CH$_3$ | OC$_2$H$_4$—OC$_3$H$_7$-i*) | 2,4-(C$_2$H$_5$)$_2$-phenyl | (Oil) |
| 304 | NH | CH$_3$ | —CH(CH$_3$)OCH$_3$ | 2-OCF$_3$-phenyl | m.p.: 109° C. |
| 305 | NH | CH$_3$ | —CH(CH$_3$)OCH$_3$ | 2-CF$_3$-phenyl | m.p.: 123° C. |
| 306 | NH | CH$_3$ | —CH(CH$_3$)OCH$_3$ | 2-COOC$_2$H$_5$-phenyl | m.p.: 132° C. |

TABLE 2-continued
Preparation examples of the compounds of the formula (I)
| Ex. No. | Q | R¹ | R² | R³ | Physical data |
|---|---|---|---|---|---|
| 307 | NH | $CH_3$ | 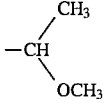 | 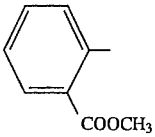 | m.p.: 129° C. |
| 308 | NH | $CH_3$ | $OC_2H_4-OC_2H_5$*⁾ | 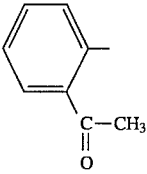 | m.p.: 103° C. |
| 309 | NH | $CH_3$ | $OC_2H_4-OCH_3$*⁾ | 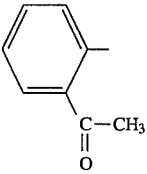 | m.p.: 85° C. |
| 310 | NH | $CH_3$ | $OC_2H_4-OC_3H_7\text{-}i$*⁾ | 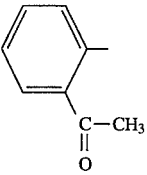 | m.p.: 91° C. |
| 311 | NH | $CH_3$ | 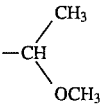 | 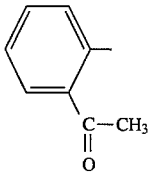 | m.p.: 112° C. |
| 312 | NH | $CH_3$ | $OCH_3$ | 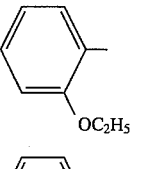 | m.p.: 146° C. |
| 313 | NH | $CH_3$ | $SC_2H_5$ | 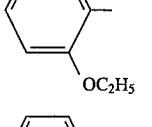 | m.p.: 126° C. |
| 314 | NH | $CH_3$ | $OCH_3$ | 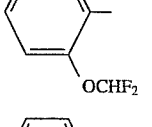 | m.p.: 133° C. |
| 315 | m.p. | $CH_3$ | $OCH_3$ | 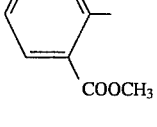 | m.p.: 163° C. |

TABLE 2-continued

Preparation examples of the compounds of the formula (I)

| Ex. No. | Q | R¹ | R² | R³ | Physical data |
|---|---|---|---|---|---|
| 316 | NH | $CH_3$ | $OCH_3$ | 2-($COOC_2H_5$)phenyl | m.p.: 146° C. |
| 317 | NH | $CH_3$ | $SC_2H_5$ | 2-($COOCH_3$)phenyl | m.p.: 152° C. |
| 318 | NH | $CH_3$ | Cl | 2-($COOCH_3$)phenyl | m.p.: 147° C. |
| 319 | NH | $CH_3$ | Br | 2-($COOCH_3$)phenyl | m.p.: 148° C. |
| 320 | NH | cyclopropyl | Br | 2-($COOCH_3$)phenyl | m.p.: 153° C. |
| 321 | NH | cyclopropyl | Cl | 2-($COOCH_3$)phenyl | m.p.: 155° C. |
| 322 | NH | $CH_3$ | $SC_2H_5$ | 2-($COOC_2H_5$)phenyl | m.p.: 137° C. |
| 323 | NH | cyclopropyl | $SCH_3$ | 2-($COOCH_3$)phenyl | m.p.: 166° C. |
| 324 | NH | cyclopropyl | $SC_2H_5$ | 2-($COOCH_3$)phenyl | m.p.: 159° C. |
| 325 | NH | $-NHCOO-C_2H_5$*⁾ | $OCH_3$ | 2-($COOCH_3$)phenyl | |

TABLE 2-continued

Preparation examples of the compounds of the formula (I)

| Ex. No. | Q | R¹ | R² | R³ | Physical data |
|---------|-----|------------------|------|--------------|---------------|
| 326 | NH | —NHCOO—<br>C₂H₅*⁾ | OCH₃ | 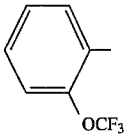 | |

*) $\dfrac{OC_2H_4-}{OC_2H_5} = -OCH_2CH_2OCH_2CH_3;\quad \dfrac{OC_2H_4-}{OCH_3} = -OCH_2CH_2OCH_3;$ $\dfrac{OC_2H_4-}{OC_3H_7\text{-}i} = -OCH_2CH_2OCH(CH_3)_2;$ $\dfrac{-NHCOO-}{C_2H_5} = -NHCOOCH_2CH_3.$ The compound shown in Table 2 as Example 183 may, for example, also be prepared as follows [Process (c)]:

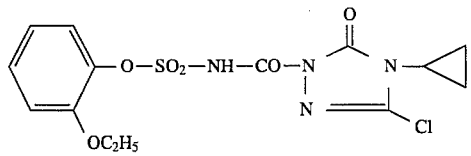

2.0 g (12.5 mmol) of 4-cyclopropyl-5-chloro-2,4-dihydro-3H-1,2,4-triazol-3-one are dissolved in 40 ml of acetonitrile, and 4.3 g (26.9 mmol) of (2-ethoxy-phenoxy)sulphonyl isocyanate are added, with stirring. The reaction mixture is stirred for 6 hours at 20° C. It is then concentrated in vacuo, the residue is stirred with diethyl ether, and the crystalline product is isolated by filtration with suction.

4.9 g (97% of theory) of 2-(2-ethoxy-phenyloxy)-sulphonylaminocarbonyl-4-cyclopropyl-5-chloro-2,4-dihydro-3H-1,2,4-triazol-3-one of melting point 121° C. are obtained. Starting substances of the formula (II)

EXAMPLE (II-1)

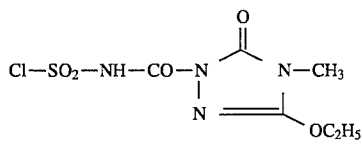

28.8 g (0.20 mol) of 5-ethoxy-4-methyl-2,4-dihydro-3H-1,2,4-triazol-3-one are introduced into 250 ml of methylene chloride, and the mixture is cooled to –10° C. 28.3 g (0.20 mol) of chlorosulphonyl isocyanate are added to this mixture, and the reaction mixture is stirred for 30 minutes without cooling. The solvent is then carefully removed by distillation under water pump vacuum.

53 g (93% of theory) of 2-chlorosulphonylaminocarbonyl-5-ethoxy-4-methyl-2,4-dihydro-3H-1,2,4-triazol-3-one are obtained as a crystalline residue of melting point 106° C.

EXAMPLE (II-2)

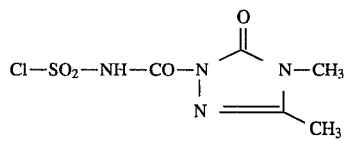

22.6 g (0.20 mol) of 4,5-dimethyl-2,4-dihydro-3H-1,2,4-triazol-3-one are introduced into 250 ml of methylene chloride and the mixture is cooled to –10° C. Then, 28.3 g (0.20 mol) of chlorosulphonyl isocyanate are added, and the mixture is stirred for 20 minutes at –5° C. to –10° C., a clear solution first being formed and the product then separating out as crystals. This product is isolated by filtration with suction.

45 g (88% of theory) of 2-chlorosulphonylaminocarbonyl-4,5-dimethyl-2,4-dihydro-3H-1,2,4-triazol-3-one of melting point 150° C. (with decomposition) are obtained.

EXAMPLE (II-3)

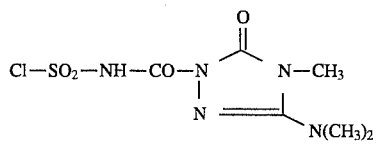

9.9 g (72 mmol) of chlorosulphonyl isocynate are slowly added at –10° C. to 0° C. to 10 g (72 mmol) of 5-dimethylamino-4-methyl-2,4-dihydro-3H-1,2,4-triazol-3-one in 250 ml of methylene chloride. After the reaction mixture has been stirred for thirty minutes, it has come to room temperature (20° C.). Then, the solvent is removed by distillation under water pump vacuum.

19.1 g (94% of theory) of 2-chlorosulphonylaminocarbonyl-5-dimethylamino-4-methyl-2,4-dihydro-3H-1,2,4-triazol-3-one are obtained as an amorphous residue.

Use Examples:

In the use examples, compound (A) below is used as comparison substance:

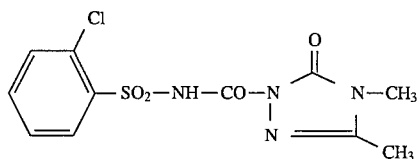

(A)

2-(2-Chloro-phenylsulphonylaminocarbonyl)-4,5-dimethyl-2,4-dihydro-3H-1,2,4-triazol-3-one (disclosed in EP-A 341 489).

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

A clearly superior activity compared with the prior art is shown, in this test, for example by the compounds of the following preparation examples: 2, 4, 13, 33, 39, 41, 43, 45, 58, 64 and 65.

TABLE A

| | Pre-emergence test/greenhouse | | | | | |
|---|---|---|---|---|---|---|
| Active compound | Application rate (g/ha) | Wheat | Amaranthus | Galinsoga | Matricaria | Stellaria |
| (A) (known) | 250 | 0 | 0 | 0 | 0 | 0 |
| (13) | 250 | 70 | 90 | 95 | 95 | 80 |
| (4) × N(C₂H₅)₃ | 250 | 0 | 70 | 70 | 90 | 60 |
| (33) | 250 | 0 | 95 | 95 | 90 | 90 |
| (2) | 250 | 20 | 95 | 95 | 90 | 80 |

TABLE A-continued

Pre-emergence test/greenhouse

| Active compound | Application rate (g/ha) | Wheat | Amaranthus | Galinsoga | Matricaria | Stellaria |
|---|---|---|---|---|---|---|
| (39) 2-C₂H₅-C₆H₄-NH-SO₂-NH-CO-N(COCH₃)-N=C(OC₂H₅)(NCH₃) | 250 | 0 | 80 | 95 | 80 | 50 |
| (41) 2-OCH₃-C₆H₄-NH-SO₂-NH-CO-N(COCH₃)-N=C(OC₂H₅)(NCH₃) | 250 | 0 | 30 | 95 | 95 | 90 |
| (43) 2-OCF₃-C₆H₄-NH-SO₂-NH-CO-N(COCH₃)-N=C(OC₂H₅)(NCH₃) | 250 | 0 | 90 | 95 | 95 | 90 |
| (43) 2-OCF₃-C₆H₄-NH-SO₂-NH-CO-N(COCH₃)-N=C(OC₂H₅)(NCH₃) | 250 | 0 | 95 | 95 | 95 | 95 |
| (58) 2-Cl,6-C₂H₅-C₆H₃-NH-SO₂-NH-CO-N(COCH₃)-N=C(OC₂H₅)(NCH₃) | 250 | 0 | — | 95 | 95 | 70 |
| (64) 2-COCH₃-C₆H₄-NH-SO₂-NH-CO-N(COCH₃)-N=C(OC₂H₅)(NCH₃) | 250 | 30 | 95 | 95 | 60 | 60 |
| (65) 2-OCH₃-C₆H₄-N(CH₃)-SO₂-NH-CO-N(COCH₃)-N=C(OC₂H₅)(NCH₃) | 250 | 0 | 100 | 95 | 95 | 70 |

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)

100%=total destruction

A clearly superior activity compared with the prior art is shown, in this test, for example by the compounds of the following preparation examples: 2, 4, 13, 14, 33, 39, 41 and 43.

TABLE B

| Active compound | Post-emergence test/greenhouse | | | | | | | |
|---|---|---|---|---|---|---|---|---|
| | Application rate (g/ha) | Wheat | Abutilon | Galinsoga | Ipomoea | Matricaria | Solanum | Xanthium |
| 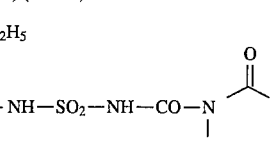 (A) (known) | 250 | 0 | 0 | 0 | 0 | 0 | 70 | 0 |
| 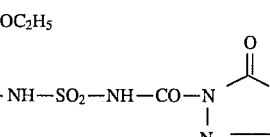 (13) | 250 | 0 | 95 | 100 | 95 | 100 | 95 | 100 |
| 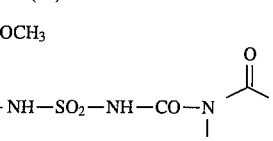 (14) | 250 | 0 | 40 | 50 | 40 | 30 | 90 | 95 |
| 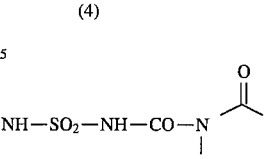 × N(C$_2$H$_5$)$_3$ (4) | 250 | 0 | 70 | 90 | 80 | 30 | 95 | 100 |
| 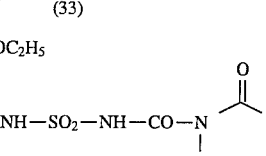 (33) | 250 | 0 | 90 | 100 | 70 | 90 | 95 | 90 |
| 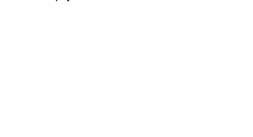 (2) | 250 | 0 | 80 | 100 | 90 | 90 | 95 | 100 |

TABLE B-continued

Post-emergence test/greenhouse

| Active compound | Application rate (g/ha) | Wheat | Abutilon | Galinsoga | Ipomoea | Matricaria | Solanum | Xanthium |
|---|---|---|---|---|---|---|---|---|
| (39) 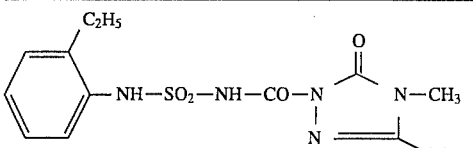 | 250 | 0 | 60 | 95 | 60 | 80 | 90 | 100 |
| (41) 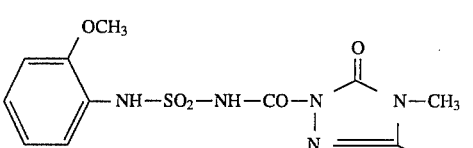 | 250 | 0 | 100 | 100 | 80 | 100 | 100 | 100 |
| (43) 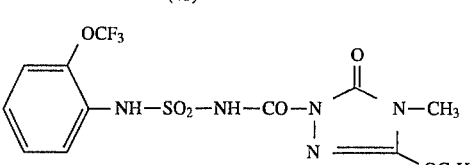 | 250 | 0 | 95 | 100 | 80 | 100 | 100 | 100 |

We claim:

1. A sulphonylaminocarbonyltriazoline of the formula

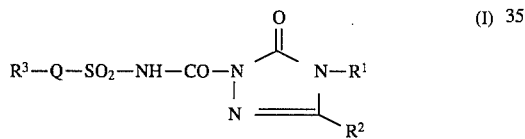

in which

Q represents oxygen, sulphur or one of the following groups

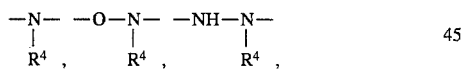

$R^1$ represents hydrogen, hydroxyl, amino, or represents $C_2$–$C_{10}$-alkylideneamino, or represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, or represents $C_3$–$C_6$-alkenyl or $C_3$–$C_6$-alkinyl, each of which is optionally substituted by fluorine, chlorine or bromine, or represents $C_3$–$C_6$-cycloalkyl which is optionally substituted by fluorine, chlorine, bromine and/or $C_1$–$C_4$-alkyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy or $C_1$–$C_4$-alkoxy-carbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- or chlorine-substituted $C_1$–$C_3$-alkylthio, $C_1$–$C_4$-alkylsulphinyl, $C_1$–$C_4$-alkylsulphonyl or $C_1$–$C_4$-alkoxy-carbonyl, or represents $C_1$–$C_6$-alkoxy which is optionally substituted by fluorine, chlorine, cyano, phenyl, $C_1$–$C_4$-alkoxy or $C_1$–$C_4$-alkoxy-carbonyl, or represents $C_3$–$C_6$-alkenyloxy, or represents $C_1$–$C_4$-alkylamino, $C_3$–$C_6$-cycloalkylamino or di($C_1$–$C_4$-alkyl)-amino, each of which is optionally substituted by fluorine, cyano, $C_1$–$C_4$-alkoxy or $C_1$–$C_4$-alkoxy-carbonyl, or represents $C_1$–$C_6$-alkanoylamino, or represents $C_1$–$C_6$-alkoxycarbonylamino, $R^2$ represents hydrogen, hydroxyl, mercapto, amino, halogen, or represents $C_1$–$C_6$-alkyl or $C_2$–$C_6$-alkenyl, optionally substituted by fluorine, chlorine, bromine cyano, $C_3$–$C_6$-cycloalkyl, $C_1$–$C_4$-alkoxy, $C_1$–$C_4$-alkylthio or $C_1$–$C_4$-alkoxy-carbonyl, or represents $C_3$–$C_6$-cycloalkyl which is optionally substituted by fluorine, chlorine, bromine or $C_1$–$C_4$-alkyl, or represents cyclohexenyl, or represents phenyl-$C_1$–$C_3$-alkyl which is optionally substituted by fluorine, chlorine, bromine, cyano, nitro, $C_1$–$C_4$-alkyl, trifluoromethyl, $C_1$–$C_4$-alkoxy or $C_1$–$C_4$-alkoxycarbonyl, or represents phenyl which is optionally substituted by fluorine, chlorine, bromine, cyano, nitro, $C_1$–$C_4$-alkyl, trifluoromethyl, $C_1$–$C_4$-alkoxy, fluorine- or chlorine-substituted $C_1$–$C_3$-alkoxy, $C_1$–$C_4$-alkylthio, fluorine- or chlorine-substituted $C_1$–$C_3$-alkylthio, $C_1$–$C_4$-alkyl-sulphinyl, $C_1$–$C_4$-alkylsulphonyl and/or $C_1$–$C_4$-alkoxy-carbonyl, or represents $C_1$–$C_6$-alkoxy which is optionally substituted by fluorine, chlorine, cyano, $C_1$–$C_4$-alkoxy or $C_1$–$C_4$-alkoxy-carbonyl, or represents $C_3$–$C_6$-alkenyloxy, $C_3$–$C_6$-alkinyloxy or $C_3$–$C_6$-cycloalkyloxy, or represents phenoxy or benzyloxy, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents $C_1$–$C_6$-alkylthio, $C_1$–$C_6$-alkylsulphinyl, $C_1$–$C_6$-alkylsulphonyl, $C_3$–$C_6$-alkenylthio, $C_3$–$C_6$-alkinylthio or $C_3$–$C_6$-cycloalkylthio, each of which is optionally substituted by fluorine, chlorine, cyano, $C_1$–$C_4$-alkoxy or $C_1$–$C_4$-alkoxy-carbonyl, or represents phenylthio or benzylthio, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents $C_1$–$C_6$-alkylamino or $C_3$–$C_6$-alkenylamino, or represents phenylamino or benzylamino, each of which is optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, or represents di-($C_1$–$C_4$-alkyl)-amino, or represents aziridino, pyrrolidino or morpholino, each of which is optionally substituted by $C_1$–$C_4$-alkyl, $R^3$ represents $C_1$–$C_6$-alkyl, $C_3$–$C_6$-alkenyl or $C_3$–$C_6$-alkinyl, each of which is optionally substituted by halogen, cyano, carboxyl, $C_1$–$C_4$-alkoxy, $C_1$–$C_4$-alkylthio, $C_1$–$C_4$-alkylsulphinyl, $C_1$–$C_4$-alkylsulphonyl or $C_1$–$C_4$-alkoxy-carbonyl, or represents $C_3$–$C_6$-cycloalkyl or $C_3$–$C_6$-cycloalkyl-$C_1$–$C_4$-alkyl, each of which is optionally substituted by halogen, cyano, carboxyl, $C_1$–$C_4$-alkyl, $C_1$–$C_4$-halogenoalkyl or $C_1$–$C_4$-alkoxy-carbonyl, or represents $C_1$–$C_6$-alkylsulphonyl, $C_1$–$C_6$-alkylamirfosulphonyl or di-($C_1$–$C_4$-alkyl)-aminosulphonyl, each of which is optionally substituted by halogen, or represents phenyl, naphthyl, tetralinyl, phenyl-$C_1$–$C_4$-alkyl, naphthyl-$C_1$–$C_4$-alkyl or tetralinyl-$C_1$–$C_4$-alkyl, each of which is optionally substituted by halogen, cyano, carboxyl, nitro, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (in each case optionally substituted by halogen, cyano, $C_1$–$C_4$-alkoxy or $C_1$–$C_4$-alkoxy-carbonyl), by $C_1$–$C_4$-alkylsulphonyloxy, $C_1$–$C_4$-alkylaminosulphonyloxy, di-($C_1$–$C_4$-alkyl)aminosulphonyloxy, $C_1$–$C_4$-halogenoalkylsulphonyloxy, di-($C_1$–$C_4$-alkyl)aminocarbonyl or $C_1$–$C_4$-alkylaminocarbonyloxy, by $C_3$–$C_6$-cycloalkyl or $C_3$–$C_6$-cycloalkyl-$C_1$–$C_4$-alkyl (in each case optionally substituted by halogen or $C_1$–$C_4$-alkyl), by phenyl, phenoxy, phenylthio, phenylsulphinyl, phenylsulphonyl, phenylsulphonyloxy, phenylamino, phenylcarbonyl or phenyl-$C_1$–$C_4$-alkyl (in each case optionally substituted by halogen, cyano, nitro, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkoxycarbonyl or $C_1$–$C_4$-alkoxy-amino), by $C_1$–$C_4$-alkyl-carbonyl, $C_3$–$C_6$-cycloalkylcarbonyl or $C_1$–$C_4$-alkoxy-carbonyl (in each case optionally substituted by halogen, $C_3$–$C_6$-cycloalkyl or $C_1$–$C_4$-alkoxy), $R^4$ represents hydrogen, hydroxyl, amino, cyano, or represents $C_1$–$C_6$-alkyl, $C_3$–$C_6$-alkenyl or $C_3$–$C_6$-alkinyl, each of which is optionally substituted by halogen, cyano, carboxyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylamino, di($C_1$–$C_4$-alkyl)-amino or $C_1$–$C_4$-alkoxy-carbonyl, or represents $C_1$–$C_4$-alkoxy-carbonyl, or represents $C_1$–$C_6$-alkoxy, $C_3$–$C_6$-alkenyloxy, benzyloxy, phenoxy or di-($C_1$–$C_4$-alkoxy)-(thio)-phosphoryl, or represents the following group $Q^1$—$R^5$ in which $Q^1$ represents —CO— or —$SO_2$— and $R^5$ represents $C_1$–$C_6$-alkyl which is optionally substituted by halogen or $C_1$–$C_4$-alkoxy, or represents $C_3$–$C_6$-cycloalkyl which is phenyl which is optionally substituted by halogen, or $C_1$–$C_4$-alkyl, or represents phenyl which is optionally substituted by halogen, $C_1$–$C_4$-alkyl, $C_1$–$C_4$-halogenoalkyl or $C_1$–$C_4$-alkoxy, or a salt thereof.

2. A compound or salt thereof according to claim 1, in which

Q represents oxygen or the group

$R^1$ represents hydrogen, hydroxyl, amino, or represents $C_3$–$C_8$-alkylideneamino, or represents methyl, ethyl, n- or i-propyl, n-, i-, so or t-butyl, dichloromethyl, fluoroethyl, chloroethyl, difluoroethyl, dichloroethyl, trifluoroethyl, trichloroethyl, chlorodifluoromethyl, tetrafluoroethyl, cyanomethyl, cyanoethyl, methoxymethyl, ethoxymethyl, methoxyethyl, ethoxyethyl, or represents allyl, chloroallyl, dichloroallyl, propargyl, or represents chloropropyl, benzyl or phenyl, or represents methoxy, ethoxy, n- or i-propoxy, or represents allyloxy, n- or i- or s-butoxy, or represents methylamino, ethylamino, n- or i-propylamino, or represents cyclopropylamino, dimethylamino, diethylamino, acetylamino, methoxycarbonylamino or ethoxycarbonylamino, $R^2$ represents hydrogen, hydroxyl, mercapto, amino, fluorine, chlorine, bromine, or represents methyl, ethyl, n- or i-propyl, n-, i-, s- or t-butyl, difluoromethyl, trifluoromethyl, dichloromethyl, trichloromethyl, cyanomethyl, cyanoethyl, cyclopropylmethyl, methoxymethyl, ethoxymethyl, methoxyethyl, ethoxyethyl, methylthiomethyl, ethylthiomethyl, methylthioethyl or ethylthioethyl, or represents cyclopropyl, difluorocyclopropyl or dichlorocyclopropyl, or represents phenyl or benzyl, or represents methoxy, ethoxy, n- or i-propoxy, or represents methoxymethoxy, ethoxymethoxy, methoxyethoxy or ethoxyethoxy, or represents phenoxy or benzyloxy, or represents methylthio, ethylthio, n- or i-propylthio, allylthio, propargylthio, cyclopropylmethylthio, methylsulphinyl, ethylsulphinyl, methylsulphonyl, ethylsulphonyl, phenylthio or benzylthio, or represents methylamino, ethyiamino, n- or i-propylamino, phenylamino or benzylamino, or represents dimethylamino, diethylamino, dipropylamino, methylethylamino, methylpropylamino, or represents aziridino, or represents pyrrolidino, piperidino or morpholino, each of which is optionally substituted by methyl or ethyl, $R^3$ represents methyl, ethyl, no or i-propyl or n-, i-, s- or t-butyl, each of which is optionally substituted by fluorine, chlorine, cyano, methoxy, ethoxy, methoxycarbonyl or ethoxycarbonyl, or represents cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl or cyclohexylethyl, each of which is optionally substituted by fluorine, chlorine, cyano, methyl, ethyl, trifluoromethyl, methoxycarbonyl or ethoxycarbonyl, or represents methylsulphonyl, ethylsulphonyl, propylsulphonyl or butylsulphonyl, optionally substituted by fluorine or chlorine, or represents phenyl which is optionally substituted by fluorine, chlorine, bromine, cyano, carboxyl, nitro, by methyl, ethyl, methoxy, ethoxy, methylthio, ethylthio, methylsulphinyl, ethylsulphinyl, methylsulphonyl or ethylsulphonyl (in each case optionally substituted by fluorine, chlorine, cyano, methoxy, ethoxy, methoxycarbonyl or ethoxycarbonyl), by methylsulphonyloxy, ethylsulphonyloxy, methylaminosulphonyloxy, ethylaminosulphonyloxy, dimethylaminosulphonyloxy, diethylaminosulphonyloxy, trifluoromethylsulphonyloxy, dimethylaminocarbonyl or diethylaminocarbonyl, by cyclohexyl or cyclohexylmethyl (in each case optionally substituted by chlorine, methyl or ethyl), by phenyl, phenoxy, phenylthio, phenylsulphonyl, phenylsulphonyloxy, phenylamino, phenylcarbonyl, phenylmethyl or phenylethyl (in each case optionally substituted by fluorine, chlorine, cyano, nitro, methyl, ethyl, trifluoromethyl, methoxy, ethoxy, difluoromethoxy, trifluoromethoxy, methylthio, ethylthio, trifluoromethylthio, methoxycarbonyl or ethoxycarbonyl), by acetyl, cyclopropylcarbonyl, methoxycarbonyl or ethoxycarbonyl (optionally substituted by fluorine, chlorine, cyclopentyl, cyclohexyl, methoxy or ethoxy), or represents naphthyl or tetralinyl, each of which is optionally substituted by fluorine, chlorine, cyano, nitro, methyl, ethyl, methoxy or ethoxy, or represents naphthylmethyl, naphthylethyl, tetralinylmethyl or tetralinylethyl, each of which is optionally substituted by fluorine, chlorine, methyl, ethyl, methoxy or ethoxy, $R^4$ represents hydrogen, cyano, cyanomethyl, cyanoethyl, difluoromethyl, methoxymethyl, ethoxymethyl, methoxyethyl, ethoxyethyl, methoxycarbonylmethyl, ethoxycarbonylmethyl, methoxycarbonylethyl, ethoxycarbonylethyl, allyl, propargyl, methoxycarbonyl, ethoxycarbonyl, methoxy, ethoxy, allyloxy or benzyloxy, or represents the group $Q^1$—$R^5$ in which $Q^1$ represents —CO— or —$SO_2$— and $R^5$ represents methyl, ethyl or propyl, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl or ethyl, or represents phenyl which is optionally substituted by fluorine, chlorine, bromine, methyl, ethyl, trifluoromethyl, methoxy or ethoxy.

3. A compound according to claim 1, which is the sodium, potassium, magnesium, calcium, ammonium, $C_1$–$C_4$-alkyl-ammonium, di-($C_1$–$C_4$-alkyl)-ammonium, tri-(($C_1$–$C_4$-alkyl)-ammonium, $C_5$- or $C_6$-cycloalkyl-ammonium or di-($C_1$–$C_2$-alkyl0-benzyl-ammonium salt of a compound of the formula I.

4. A herbicidal composition comprising a herbicidally effective amount of a compound or salt thereof according to claim 1 and a diluent.

5. A method of combatting unwanted vegetation which comprises applying to such vegetation or to a locus from which it is desired to exclude such vegetation a herbicidally effective amount of a compound or salt thereof according to claim 1.

* * * * *

UNITED STATES PATENT AND TRADEMARK OFFICE
CERTIFICATE OF CORRECTION

PATENT NO.  : 5,552,369
DATED       : September 3, 1996
INVENTOR(S) : Findeisen, et al.

It is certified that error appears in the above-indentified patent and that said Letters Patent is hereby corrected as shown below:

| | |
|---|---|
| Col. 91, line 26 | Delete " $C_1$-$C_6$-alkylamirfosulphonyl " and substitute -- $C_1$-$C_6$-alkylamino-sulphonyl -- |
| Col. 92, line 1 | Delete " which is phenyl " |
| Col. 92, line 17 | Delete " so " and substitute -- s- -- |
| Col. 92, line 46 | Delete " ethyiamino " and substitute -- ethylamino -- |
| Col. 94, line 19 | Delete " di-($C_1$-$C_2$-alkyl0-benzyl-ammonium " and substitute -- di-($C_1$-$C_2$-alkyl)-benzyl-ammonium -- |

Signed and Sealed this

Twenty-fifth Day of March, 1997

Attest:

BRUCE LEHMAN

*Attesting Officer*     *Commissioner of Patents and Trademarks*